(12) United States Patent
Schulze

(10) Patent No.: US 8,114,080 B2
(45) Date of Patent: Feb. 14, 2012

(54) FLEXIBLE BONE FIXATION DEVICE

(75) Inventor: Dale R. Schulze, Warsaw, IN (US)

(73) Assignee: DePuy Products, Inc., Warsaw, IN (US)

( * ) Notice: Subject to any disclaimer, the term of this patent is extended or adjusted under 35 U.S.C. 154(b) by 565 days.

(21) Appl. No.: 11/900,896

(22) Filed: Sep. 13, 2007

(65) Prior Publication Data

US 2008/0077133 A1    Mar. 27, 2008

Related U.S. Application Data

(63) Continuation-in-part of application No. 11/527,951, filed on Sep. 27, 2006, now Pat. No. 7,842,037.

(51) Int. Cl.
  *A61B 17/56* (2006.01)
  *A61B 17/80* (2006.01)
(52) U.S. Cl. ........... 606/70; 606/280; 606/284; 606/285
(58) Field of Classification Search ............ 606/66, 606/70–71, 74, 280–299, 250–260, 263–264; 623/17.11–17.16
  See application file for complete search history.

(56) References Cited

U.S. PATENT DOCUMENTS

| | | | |
|---|---|---|---|
| 2,406,832 A | | 9/1946 | Hardinge |
| 2,443,363 A | | 6/1948 | Townsend et al. |
| 3,842,825 A | | 10/1974 | Wagner |
| 4,920,959 A | * | 5/1990 | Witzel et al. ................. 606/53 |
| 5,364,398 A | | 11/1994 | Chapman et al. |
| 5,462,547 A | | 10/1995 | Weigum |
| 5,527,310 A | | 6/1996 | Cole et al. |
| 5,558,674 A | | 9/1996 | Heggeness et al. |
| 5,766,175 A | | 6/1998 | Martinotti |
| 5,800,162 A | | 9/1998 | Shimodaira et al. |
| 5,975,904 A | | 11/1999 | Spiegel |
| 6,136,002 A | * | 10/2000 | Shih et al. ..................... 606/250 |
| 6,340,362 B1 | | 1/2002 | Pierer et al. |
| 6,524,315 B1 | | 2/2003 | Selvitelli et al. |
| 6,616,669 B2 | * | 9/2003 | Ogilvie et al. ............... 606/279 |
| 6,645,207 B2 | * | 11/2003 | Dixon et al. .................. 606/261 |
| 6,706,044 B2 | * | 3/2004 | Kuslich et al. ............... 606/261 |
| 7,344,537 B1 | * | 3/2008 | Mueller ........................ 606/278 |
| 2002/0128653 A1 | | 9/2002 | Haidukewych |
| 2002/0169449 A1 | | 11/2002 | Kuslich et al. |
| 2002/0183752 A1 | * | 12/2002 | Steiner et al. ................ 606/69 |
| 2004/0039388 A1 | * | 2/2004 | Biedermann et al. ......... 606/71 |
| 2004/0102778 A1 | | 5/2004 | Huebner et al. |

(Continued)

FOREIGN PATENT DOCUMENTS

DE            101 17 426         10/2002

(Continued)

*Primary Examiner* — Thomas C. Barrett
*Assistant Examiner* — Matthew Lawson
(74) *Attorney, Agent, or Firm* — Maginot, Moore & Beck

(57) ABSTRACT

A bone fixation device bone fixation device includes a first construct comprising a plurality of first flexible plates configured to bend when a first threshold force is applied to the first construct and the plurality of first flexible plates are in an unlocked relationship and a second construct including a plurality of second flexible plates. The plurality of second flexible plates are configured to bend when a second threshold force is applied to said second construct and the plurality of second flexible plates are in an unlocked relationship. The device also includes a first locking member configured to compress first flexible plates and second flexible plates together and into a locked relationship, wherein the first threshold force applied to the first construct and the second threshold force applied to the second construct is insufficient to bend the first flexible plates and second flexible plates in the locked relationship.

25 Claims, 22 Drawing Sheets

U.S. PATENT DOCUMENTS

| | | | |
|---|---|---|---|
| 2004/0177847 A1* | 9/2004 | Foley et al. | 128/95.1 |
| 2005/0277923 A1 | 12/2005 | Sweeney | |
| 2005/0288790 A1* | 12/2005 | Swords | 623/17.19 |
| 2006/0069390 A1* | 3/2006 | Frigg et al. | 606/61 |
| 2006/0079892 A1 | 4/2006 | Roychowdhury et al. | |

FOREIGN PATENT DOCUMENTS

| | | |
|---|---|---|
| FR | 2 863 860 | 6/2005 |
| GB | 2 294 394 | 5/1996 |
| WO | WO 2007/038429 | 4/2007 |

* cited by examiner

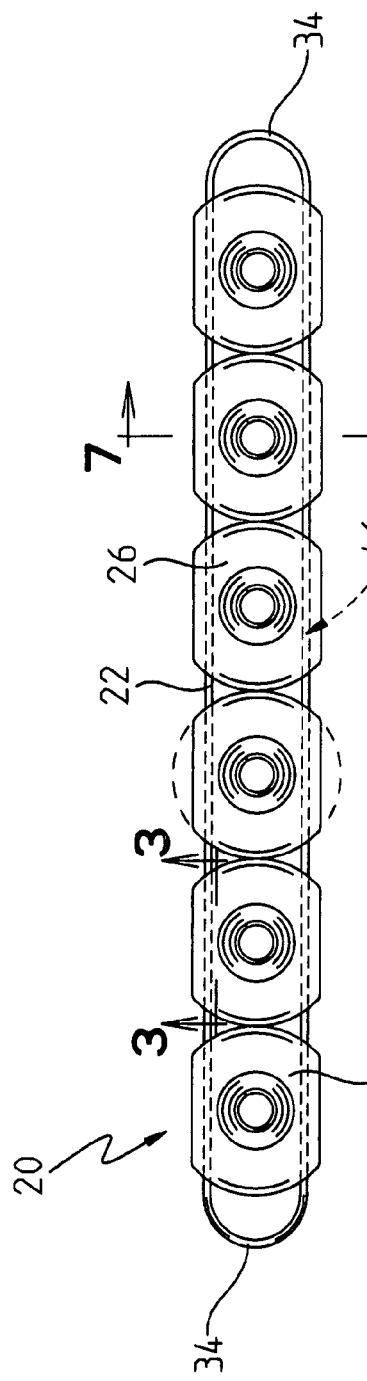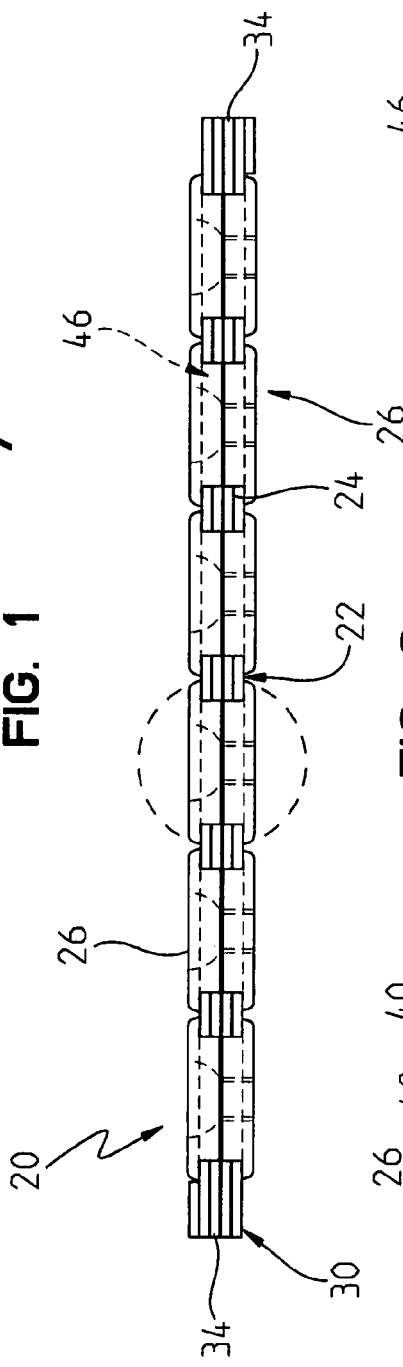

FLEXIBLE BONE FIXATION DEVICE

CROSS REFERENCE TO RELATED APPLICATIONS

This application is a Continuation-in-Part of U.S. patent application Ser. No. 11/527,951 filed Sep. 27, 2006, entitled FLEXIBLE BONE FIXATION DEVICE, the disclosure of which is herein incorporated by reference in its entirety.

FIELD

This application relates generally to the field of orthopedics, and more specifically to bone plates and systems for stabilization and compression of fractured or otherwise damaged bones.

BACKGROUND

Bone plates for internal fixation of fractured bones should generally conform to the contours of the fractured bone surface. This is especially true for compression plates that are screwed tightly against the bone. Matching the plate shape to the bone contours is important with compression plates in order to allow proper distribution of loads between the bone and the plate during healing of the fracture. It is also desirable for the plate to have a low profile and to blend with the bone surface as much as possible so as not to irritate or interfere with surrounding soft tissues, nerves, tendons, vessels, etc.

One type of bone plate for acetabular and other pelvic fractures is called a reconstruction bar. Conventional reconstruction bars are generally formed from a One type of bone plate for acetabular and other pelvic fractures is called a reconstruction bar. Conventional reconstruction bars are generally formed from a biocompatible metal that may be bent by the surgeon using special tools in order to configure the bar to conform to the bone. Typically the surgeon first forms a thin metal template by hand to conform to the bone surface at the fracture site. Working through an open incision, the surgeon bends the template to approximate the desired shape, places the template against the bone surface, removes the template, adjusts the shape of the template and repeats these steps until the template closely matches the shape of the bone surface. Then the surgeon, sometimes with the help of an assistant, uses a number of special forming tools to bend the reconstruction bar to be implanted into approximately the same configuration as the template, visually holding the bar and template side-by-side to assess when the bar is adequately similar to the template. This procedure may take several minutes of time and a significant amount of skill. The bar may then be attached to the bone using conventional cortical screws. It is not likely that the bar shape exactly matches the bone surface shape, so tightening of the bone screws may draw the bar against the bone surface, thereby inducing bending preloads at various locations along the bar due to the spring-back characteristic of the bar material. Alternatively, the bar may be implanted with significant gaps between various locations of the bar and the bone surface, resulting in the uneven transfer of loads between the bone and bar construct. Therefore, it would be advantageous to provide a reconstruction bar that may be implanted more quickly by the surgeon, requires fewer ancillary tools, is more conformable and contoured to the bone surface, and is at least as effective as a fixation device compared to conventional reconstruction bars.

Another issue currently faced by orthopedic device manufacturers is the need to provide a full line of bone plates for a large variety of bone fractures and patient anatomies. The manufacturing costs associated with forming each rigid, one-piece bone plate is significant due largely to the need to configure the plate to approximately match the bone surface shape. Furthermore, a large product inventory must be provided to the user (hospitals) to be prepared for the many types of fractures and patient anatomies to be treated. Accordingly, it would be advantageous to provide bone plates that have broader indications, where each plate may be suitable for a larger variety of fractures and patient anatomies than currently available plates. Potentially, such bone plates may be produced at lower costs than current plates and inventories reduced without compromising surgical outcomes.

SUMMARY

A bone fixation device comprises a beam including plurality of flexible members. The plurality of flexible members extend generally parallel to a curvilinear axis defined along the length of the bone fixation device. The plurality of flexible members are provided in one or more groupings that engage at least one locking member. The locking member is configured to retain the flexible members together in either a locked relationship or an unlocked relationship. In the locked relationship, the locking member compresses the flexible members together. The beam provided by the flexible members is configured to bend when a threshold force is applied to the beam, provided the flexible members are in an unlocked relationship. When the flexible members are in a locked relationship, the beam has an increased resistance to bending such that application of the threshold force is insufficient to bend the plurality of stacked flexible members and alter the shape of the bone fixation device.

In one embodiment, the at least one locking member comprises a first portion configured to engage a first side of the beam and a second portion configured to engage an opposite second side of the beam. The flexible members are arranged within the grouping in a stacked configuration. The first portion and the second portion are configured to clamp together, thus compressing the flexible members. The at least one locking member also comprises an opening extending through the first portion and the second portion. The opening is configured to receive a bone screw configured to draw the first and second portions together to clamp tightly to the flexible members while also securing the bone fixation device to the damaged bone.

The bone fixation device provides for a method of stabilizing a damaged bone. The method includes the step of providing a fixation device comprising a first construct and a second construct, wherein each of the first and second constructs include a plurality of stacked, flexible members, and wherein each of the first and second constructs have opposing ends defining an opening. The method also includes the step of providing three locking members sized for insertion into the openings, wherein each locking member includes threads for engagement into the bone. The method also includes the step of aligning one of the openings of the first construct with one of the openings of the second construct along a vertical axis. The method also includes the step of pivoting the first construct with respect to the second construct at the aligned holes while bending the first and second constructs to obtain a desired configuration, such that the fixation device conforms to the contours of the bone. The method also includes the step of inserting one of the locking members through the aligned openings and one of the locking members in each of the remaining openings, such that the locking members threadably engage the bone to attach the fixation device to the bone while holding the fixation device in the desired configuration.

In another embodiment, a bone fixation device bone fixation device includes a first construct comprising a plurality of first flexible plates configured to bend when a first threshold force is applied to the first construct and the plurality of first flexible plates are in an unlocked relationship and a second construct including a plurality of second flexible plates. The plurality of second flexible plates are configured to bend when a second threshold force is applied to said second construct and the plurality of second flexible plates are in an unlocked relationship. The device also includes a first locking member configured to compress first flexible plates and second flexible plates together and into a locked relationship, wherein the first threshold force applied to the first construct and the second threshold force applied to the second construct is insufficient to bend the first flexible plates and second flexible plates in the locked relationship.

In a further embodiment, a bone fixation device includes a first construct having a plurality of first flexible members. The plurality of first flexible members are configured to bend when a first threshold force is applied to the first construct and the plurality of first flexible members are in an unlocked relationship bone. The fixation device also includes a first locking member configured to compress the plurality of first flexible members together and into a locked relationship. The first threshold force applied to the first construct is insufficient to bend the plurality of first flexible members in the locked relationship The fixation device also includes a retainer for containing the plurality of first flexible members in a constrained relationship.

The bone fixation device further provides for a method of stabilizing a damaged bone. The method includes the step of providing a fixation device comprising a first construct and a second construct. Each of the first and second constructs include a plurality of stacked, flexible members. Each of the first and second constructs have opposing ends defining an opening. The method also includes the step of providing three locking members sized for insertion into the openings, wherein each locking member includes threads for engagement into the bone. The method includes the step of aligning one of the openings of the first construct with one of the openings of the second construct along a vertical axis and the step of pivoting the first construct with respect to the second construct at the aligned holes while bending the first and second constructs to obtain a desired configuration, such that the fixation device conforms to the contours of the bone. The method includes the step of inserting one of the locking members through the aligned openings and one of the locking members in each of the remaining openings, such that the locking members threadably engage the bone to attach the fixation device to the bone while holding the fixation device in the desired configuration.

The above described features and advantages, as well as others, will become more readily apparent to those of ordinary skill in the art by reference to the following detailed description and accompanying drawings.

BRIEF DESCRIPTION OF THE DRAWINGS

FIG. 1 shows a top view of a bone fixation device including a plurality of locking members and a beam comprised of a plurality of flexible members;

FIG. 2 shows a side view of the bone fixation device of FIG. 1;

FIG. 3 shows a cross-sectional view of one of the plurality of locking members of the bone fixation device of FIG. 1 along line III-III;

FIG. 7 shows a cross-sectional view of one of the plurality of locking members of the flexible bone plate of FIG. 1 along line VII-VII;

DESCRIPTION

With reference to FIGS. 1 and 2, an embodiment of a bone fixation device 20 is shown. The bone fixation device 20 is a bone plate/reconstruction bar which provides for internal fixation of a fractured bone. The bone fixation device 20 includes a load carrying structure/beam 22 formed from a plurality of flexible members 24. The flexible members 24 are arranged such that the device 20 is in a flexible state when relative movement between the flexible elements is permitted and in a rigid state when there is substantially no relative movement between the flexible elements. The device 20 further includes at least one locking member 26, whereby the user may apply the locking member 26 to the flexible members 24 in order to change the device 20 between the flexible and rigid states. As explained in further detail below, the device 20 may be easily shaped to conform to the contours of a fractured or otherwise damaged bone surface when the device 20 is in the flexible state. The device may then be converted to the rigid state for fixation of the fractured bone.

Figure 4:
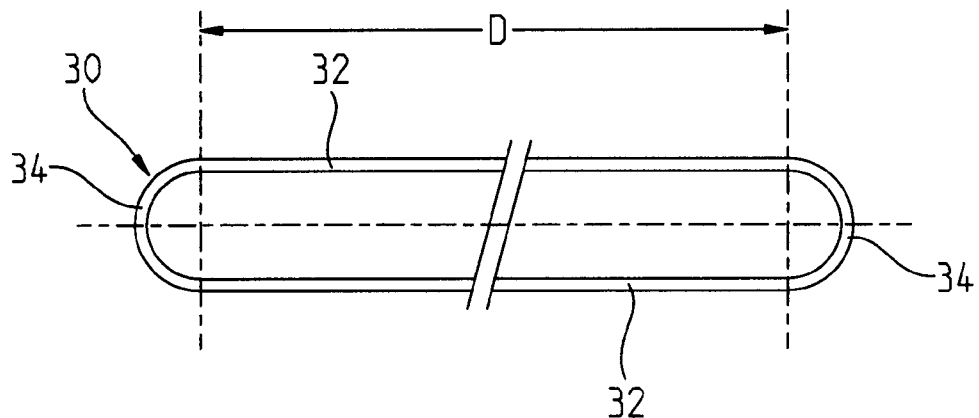
FIG. 4 shows a top view of the beam of FIG. 1.
Figure 5:
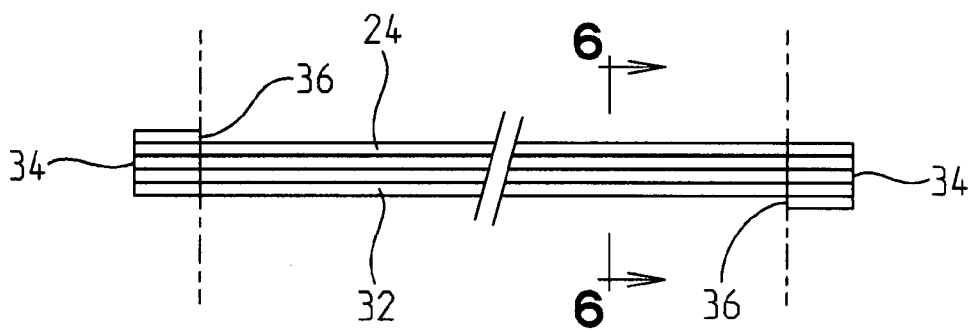
FIG. 5 shows a side view of the beam of FIG. 4.

As shown in FIGS. 4 and 5, the load carrying beam 22 of the device 20 comprises a plurality of elongate flexible members 24. In the embodiment of FIGS. 4 and 5, the flexible members 24 may be formed from a single filament, such as a metal wire, wound into an oblong coil 30. The oblong coil 30 includes two parallel spaced-apart segments 32 (also referred to herein as groupings 32) having a length D, and two rounded end turns 34 which join the segments 32 and make 180° turns in the coil 30. In this embodiment, the coil terminates in two filament ends 36. The filament ends 36 may bear against the locking members 26 near the rounded end turns 34 of the coil 30.

The filament forming the coil 30 may be formed from a spring steel, a stainless steel, a shape memory metal such as nitinol, titanium alloy, a polymer or other suitable biocompatible material. The cross-sectional shape of the filament forming the coil 30 may be any of numerous cross-sectional shapes. For example, in the embodiment of FIG. 6A, the filament comprising the coil 30 has a rectangular cross-sectional shape, and particularly a square cross-sectional shape. In the embodiment of FIG. 6B, the filament comprising the coil 30 has a rounded cross-sectional shape, and particularly a circular cross-sectional shape. Of course numerous other cross-sectional shaped filaments are possible, including other rectangular wire, such as oblong rectangular, other rounded wire, such as elliptical, and other polygonal shaped wire, such as hexagonal. Alternatively, the flexible members 24 need not be wires, but may be provided my other components, such as a plurality of stacked thin plates. Also, instead of a beam 22 with dual groupings 32, the flexible members 24 may be provided in other configurations, such as a single grouping of flexible members 24, or two or more unconnected groupings providing separate beams.

Figure 6A:
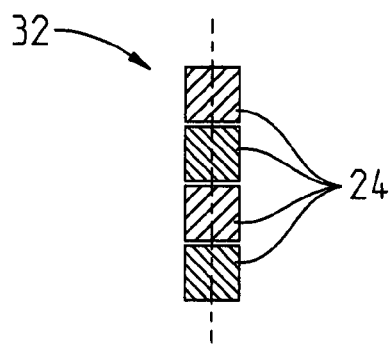
FIG. 6A shows a cross-sectional view of one embodiment of the beam of FIG. 5 along line VI-VI.
Figure 6B:
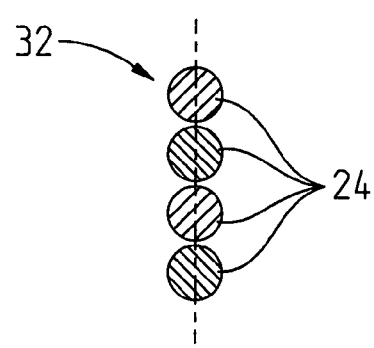
FIG. 6B shows a cross-sectional view of an alternative embodiment of the beam of FIG. 5 along line VI-VI.

As shown in FIGS. 5-6B, the elongated flexible members 24 are vertically stacked or layered in each grouping 32. An equal number of flexible members 24 are provided in each stack, such that the sum of the thicknesses (or diameters) of the flexible members 24 is the overall thickness of the load carrying structure 22. While only a single stack of flexible members 24 is shown in FIGS. 6A and 6B, two or more side-by-side stacks of flexible members may be provided in alternative embodiments.

In other embodiments, the flexible members 24 may also be arranged within each grouping in configurations other than vertical stacks. For example, the flexible members 24 may be held together in a bundled configuration having an approximately circular cross-sectional shape (not shown).

With reference again to FIGS. 1 and 2, the bone fixation device 20 also includes a plurality of locking members 26 are arranged upon the beam 22. In the disclosed embodiment, six locking members 26 are aligned end-to-end, although it is possible to have fewer or many more locking members 26, as desired. Each locking member 26 includes a top half 40 and a bottom half 42, which may be loosely attached together, such as by an integral latching element 44 (see FIG. 8). When the top half 40 and the bottom half 42 are joined, two channels 46 are formed extending through the locking member 26. The channels 46 are represented in FIGS. 1 and 2 by the dotted lines that extend through each locking member 26 between the exposed portions of the beam 22. The channels 46 in each locking member 26 provide a passage allowing the plurality of flexible members 24 of the beam 22 to extend through the locking member 26, with separate halves 40, 42 of the locking member provided on opposite sides of the beam 22. Each locking member 26 is comprised of a biocompatible material, such as, for example, metal injection molded (MIM) 316L stainless steel or any one of numerous other biocompatible metals or materials, as will be recognized by those of skill in the art.

Figure 11:
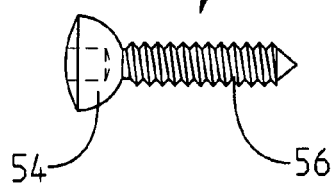
FIG. 11 shows a bone screw configured for insertion through the locking member of FIG. 8.

With reference to FIG. 7, each locking member 26 includes a bone screw hole 50 that extends through the top half 40 and the bottom half 42 of the locking member. The top half 40 of the locking member 26 includes a recess 60 that provides a concave surface 61 for receiving the head of a bone screw. The recess 60 also allows the threaded shaft of a bone screw to pass freely through to the bottom half 42. An exemplary bone screw 52 is shown in FIG. 11 and includes a head 54 with a threaded shaft 56 extending from the head 54. The bottom half 42 of the locking member 26 includes a threaded portion 70 configured to threadably engage the threaded shaft 56 of the screw 52. When the screw 52 is inserted into the hole 50, the threaded shaft 56 passes through the top half 40 of the locking member and engages the threaded portion 70 of the bottom half 42. Then, when the screw 52 is tightened, the bottom half 42 is drawn tightly against the top half 40 of the locking member 26, thereby locking the screw in the segment. Alternately, the bottom half 42 of the locking member may include an unthreaded clearance hole for the bone screw 52, such that when the bone fixation device 20 is attached to the bone using the bone screw 52, the compression against the bone surface causes the top and bottom halves to clamp together. At the same time, the bone screw serves as a fastener to attach the bone fixation device to the bone.

With reference now to FIGS. 8-10B, one embodiment of a locking member 26 is shown with the top half 40 separated from the bottom half 42. The top half 40 includes a generally planar upper surface 62 with the recess 60 leading to the hole 50 formed therein. A sidewall 64 extends from the edges of the upper surface 62 toward the bottom half 42. Slots 66 are formed within the sidewall 64 to provide for the channels 46 that extend through the locking member 26. Tabs 68 extend from the sidewall 64 toward the bottom half 42 of the locking member 26. The tabs 68 include teeth 69 on their ends that are designed to engage the bottom half 42 of the locking member and secure the top half 40 to the bottom half 42.

The bottom half 42 of the locking member 26 includes a generally planar lower surface 72 with the hole 50 extending through the lower surface 72. A sidewall 74 extends from the edges of the lower surface toward the top half 40. Slots 76 are formed within the sidewalls 74 to provide for the channels 46 to extend through the locking member 26. Grooves 78 are formed in the sidewalls 74 to receive the tabs 68 of the top half 40 of the locking member. In particular, the teeth 69 of the tabs 68 are configured to engage shelves 79 in the grooves 78 of the bottom half 42, thus loosely securing the top half to the bottom half. The arrows 58 in FIG. 8 indicate the orientation and direction in which the two halves 40, 42 may be snapped together to secure the two halves together. When the two halves 40, 42 of the locking member 26 are joined together, the slots 66 and 76 on the two halves are aligned and form openings to the channels 46 in the locking member 26. Thus, the locking member 26 may be secured to the beam 22 with the plurality of flexible members 24 extending through the channels 46 of the locking member and out the slots 66, 76.

Figure 15:
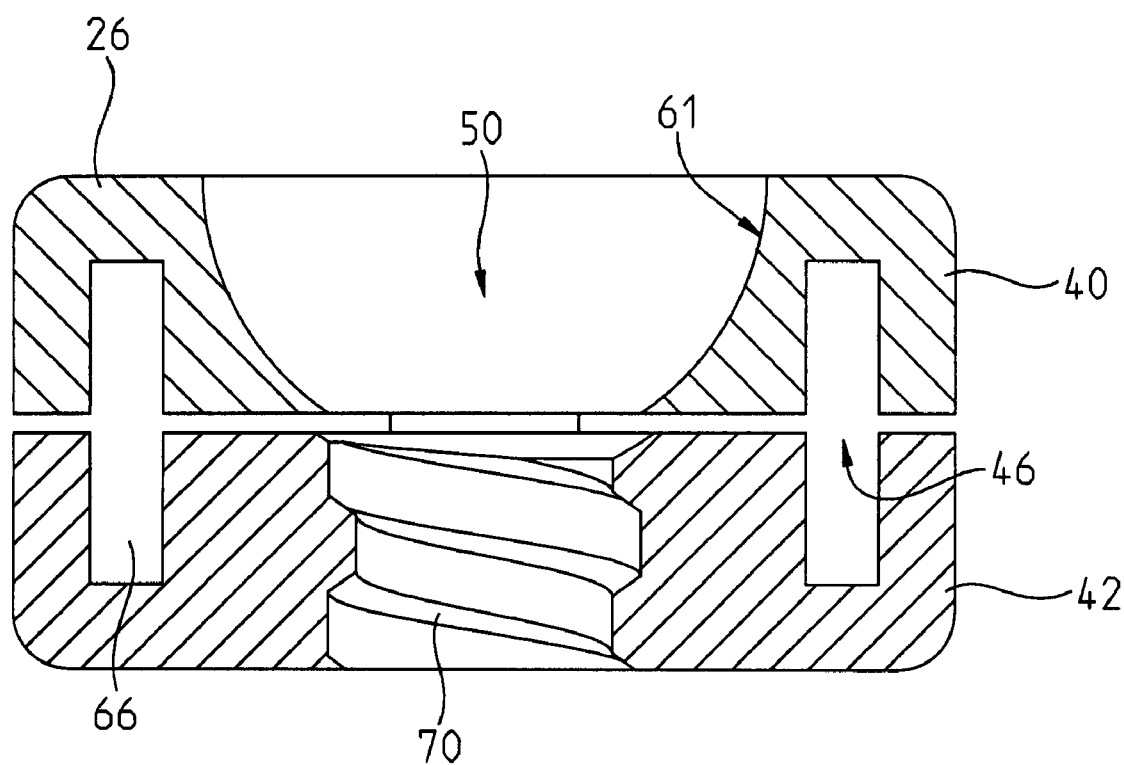
FIG. 15 shows a cross-sectional view of the locking member of FIG. 14.
Figure 16:
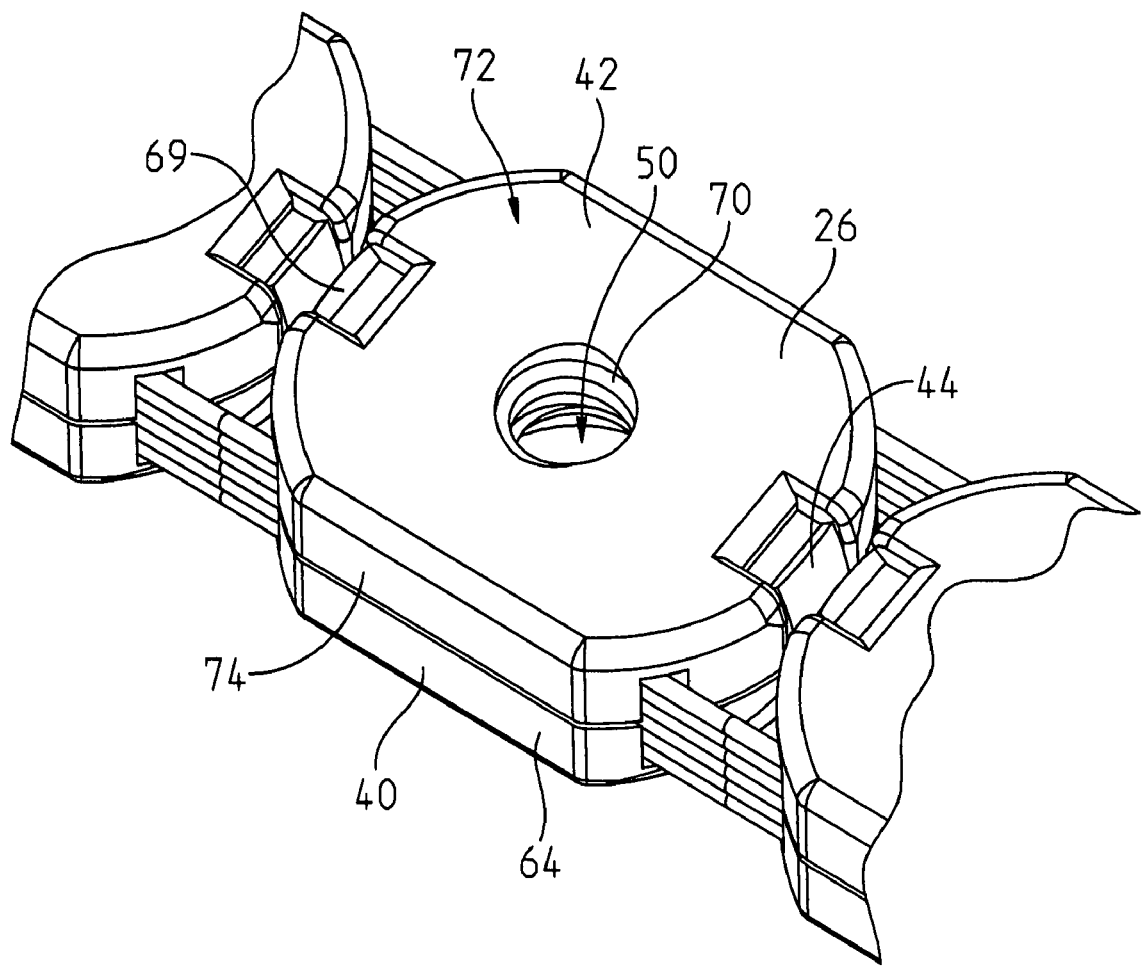
FIG. 16 shows a lower perspective view of the locking member of FIG. 14.

The channels 46 formed through a locking member 26 may include features to help maintain the locking member 26 in place upon the beam 22. For example, as shown in FIG. 3, each channel 46 may include a pair of opposing, serrated clamping surfaces 48 to help prevent movement of the flexible members 24 in the channels 46 when the bone screws are tightened. Accordingly, the serrated clamping surfaces 48 are provided to assist in preventing relative movement between the flexible elements and facilitate locking the bone fixation device 20 into a rigid condition. The serrated clamping surfaces may be provided by a ribbed, toothed or other textured surface. The channels 46 may be provided in different cross-sectional shapes dependant on the shape of the beam 22. Thus, while the channels 46 are shown with a rectangular cross-section in FIG. 7 (and FIG. 15), the channels 46 could also have a different cross-sectional shape. For example, if the beam 22 were provided as a plurality of flexible members 24 arranged in a bundled configuration, the cross-sectional shape of the channels 46 may be circular.

Figure 12A:
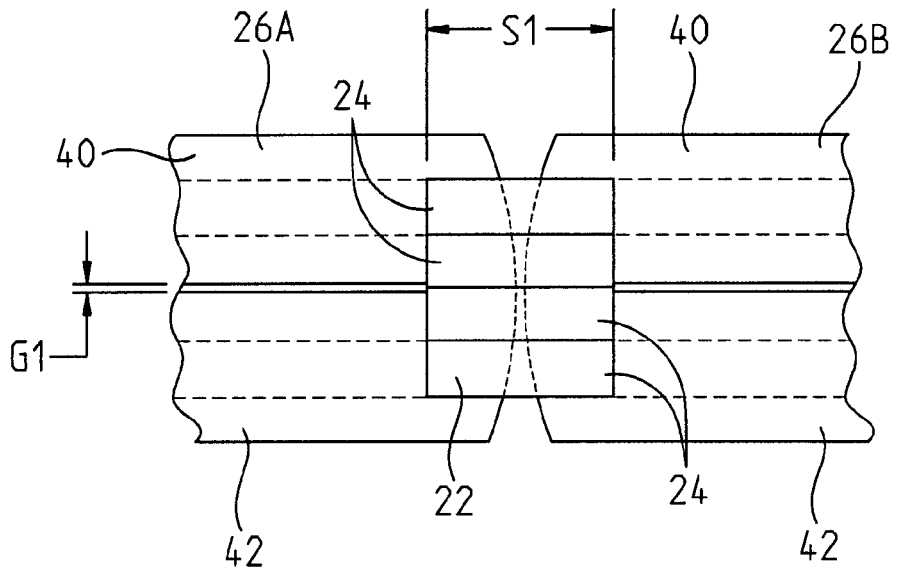
FIG. 12A shows a lateral side view of two of the plurality of locking members of FIG. 1 in an unlocked configuration.

FIG. 12A shows a detailed side view of a portion of a pair of adjacent locking members 26A, 26B with a portion of the beam 22 extending between the locking members 26A, 26B. In the embodiment of FIG. 12A, the beam 22 includes four stacked flexible members 24. When the top half 40 of the locking member 26A is loosely connected to the bottom half 42 (i.e., before tightening of the bone screw), the portion of the four flexible elements between the segments may be characterized as four individual segments having a length of S1. A gap G1 exists between the top half 40 and the bottom half 42 of the locking member 26A. This gap G1 provides a distance over which the clamping surfaces of the channels 46 of the locking member 26A may apply a clamping force on the flexible members 24.

Figure 12B:
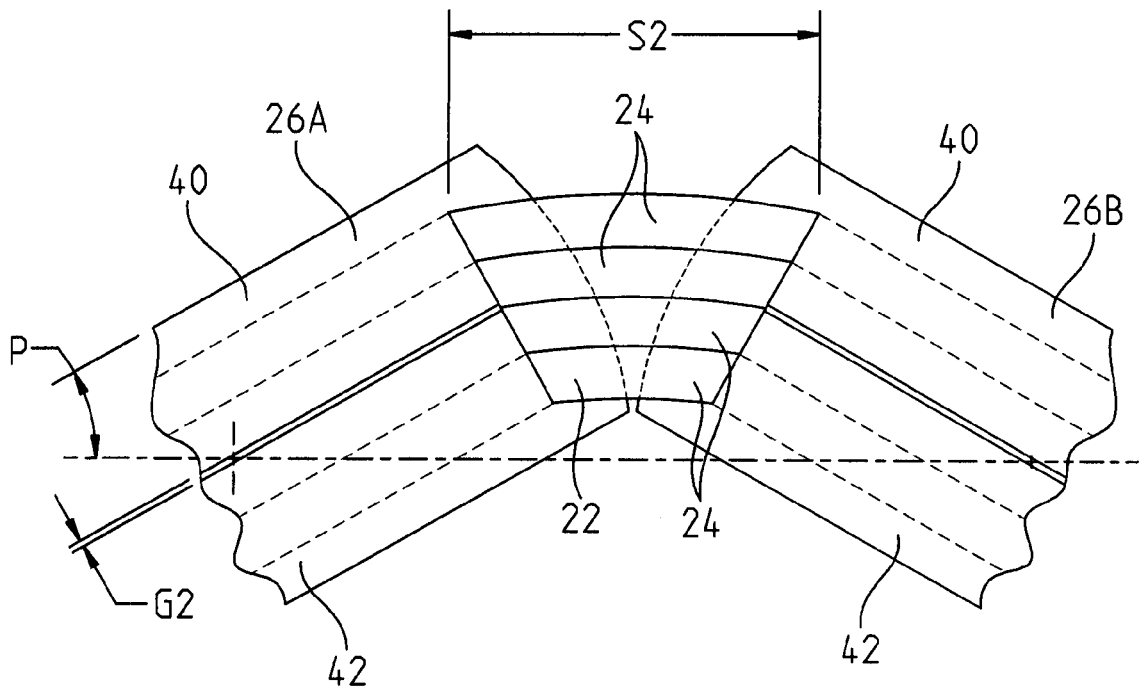
FIG. 12B shows a lateral side view of two of the plurality of locking members of FIG. 1 in a locked configuration.
Figure 13:
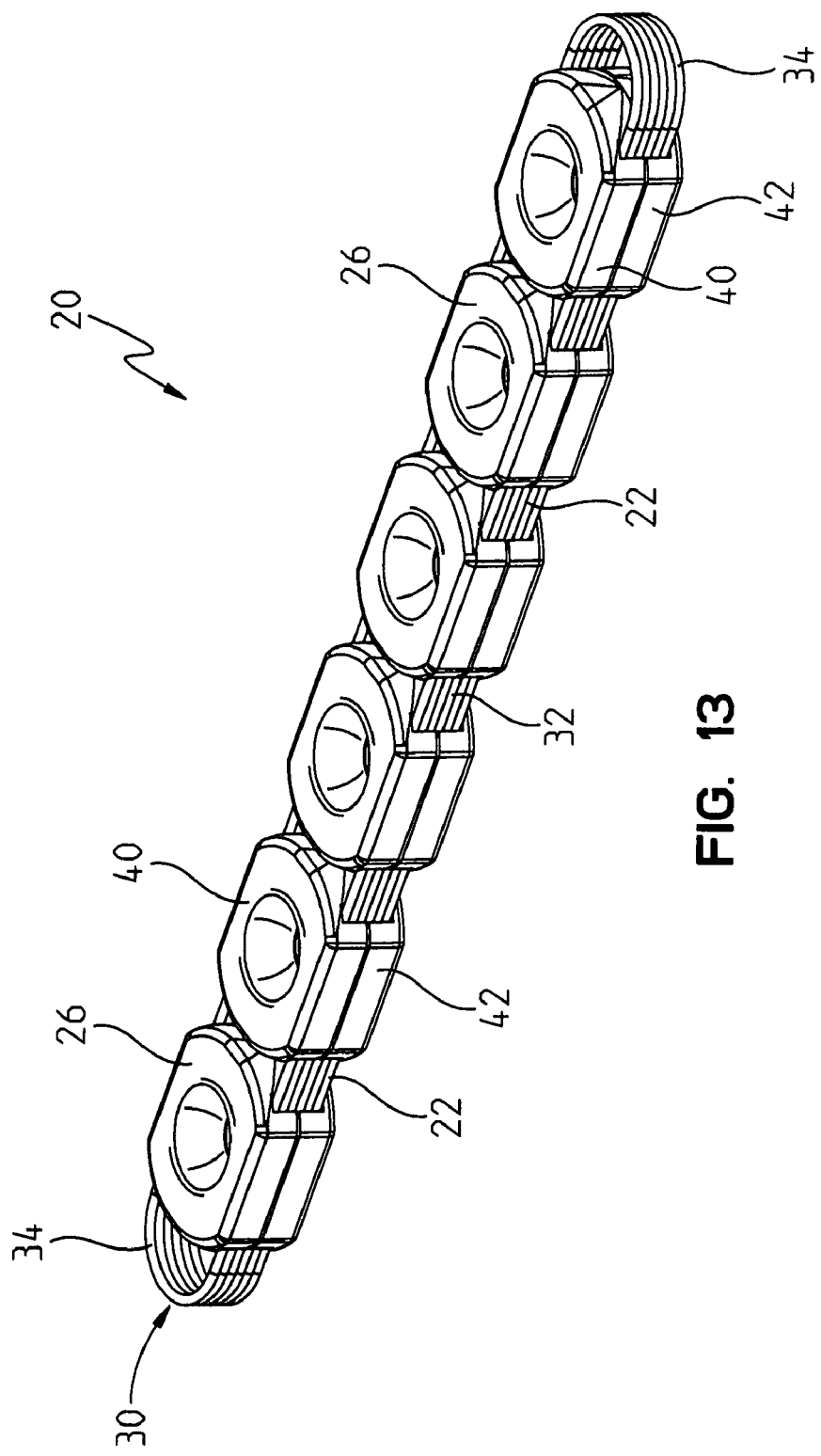
FIG. 13 shows a perspective view of an alternative embodiment of the flexible bone fixation device of FIG. 1.
Figure 14:
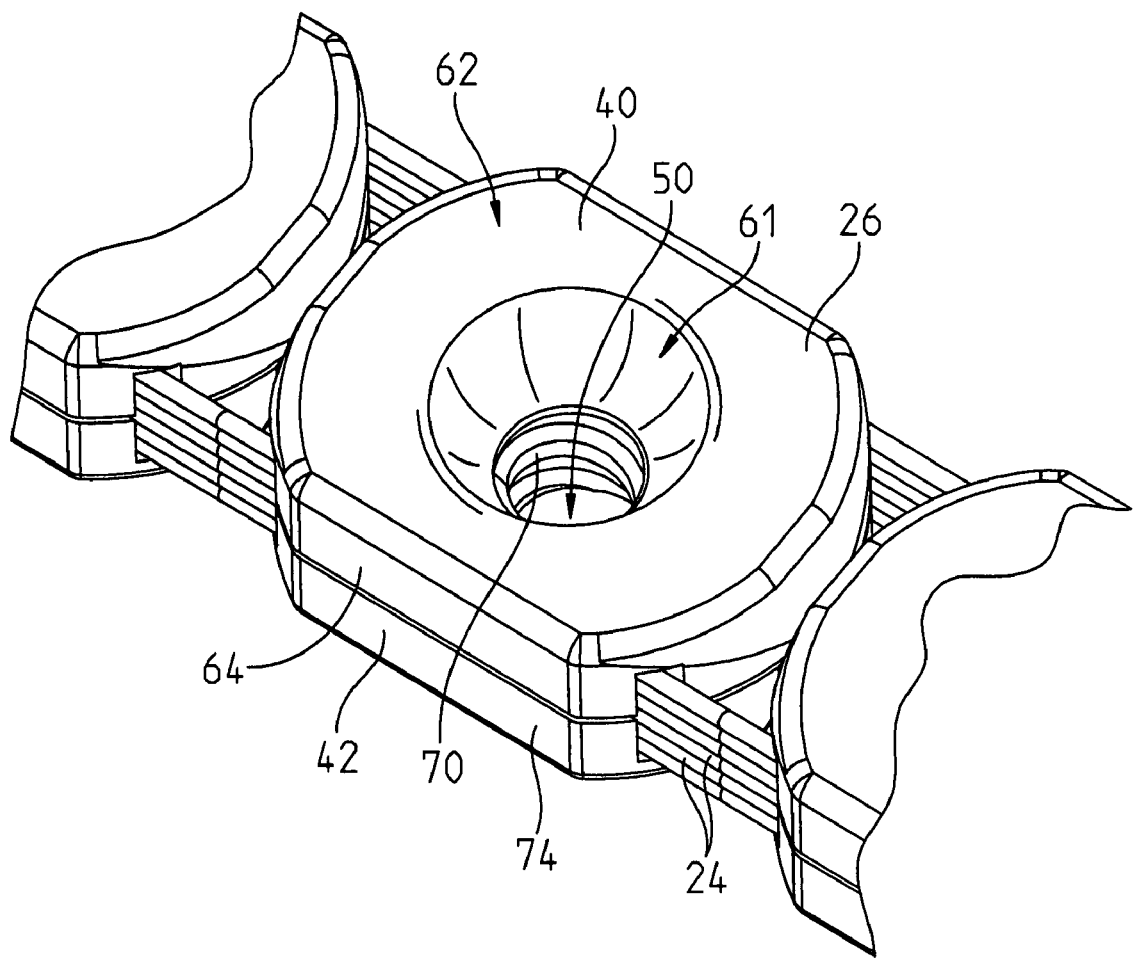
FIG. 14 shows an upper perspective view of one of the locking members of the flexible bone fixation device of FIG. 13.

FIG. 12B shows the same adjacent locking members 26A, 26B, as FIG. 12A. However, in FIG. 12B, the locking members 26A, 26B are angled relative to one another. Such angling may be necessary when the bone fixation device 10 is positioned on a contoured bone surface. In this position, the exposed portion of the flexible members 24 between the locking members 26A, 26B is generally trapezoidal in shape with a maximum dimension of S2>S1. This angled positioning between locking members 26A, 26B may be achieved when a threshold force is applied to one of the locking members 26A, 26B, thus moving the one locking member 26A relative to the other locking member 26B. The flexible quality of each of the individual flexible members 24 is defined by a moment of inertia (i.e., second moment of area) and the elasticity of the material comprised in the flexible members 24. Because of the relatively loose relationship between the flexible members, the threshold force required to bend the beam 22 is approximately equal to the aggregate bending stress for each of the plurality of flexible members 24.

When a bone screw is placed in the hole 50 of each locking member 26A, 26B, and used to compress the top half 40 of each locking member 26 toward the bottom half 42, the plurality of flexible members 24 are also compressed together. The plurality of flexible members 24 only permit a certain amount of compression, such that a gap G2 (G2<G1) still exists between the top half and the bottom half following compression by the bone screw. With the top half 40 and bottom half 42 of each locking member 26A, 26B clamping down on the flexible members 24, the flexible members 24 are fixed together and not permitted to move relative to each other, thereby greatly increasing the stiffness of the beam 22 at that location. Accordingly, the threshold force that would formerly cause the first locking member 26A to move relative to the second locking member 26B is no longer sufficient to bend the beam 22, and a much greater force is required to move the first locking member 26A relative to the second locking member 26B. This locking feature allows the flexible bone plate 20 to be bent by the hands of a human in the unlocked position by adjusting the position of adjacent locking members 26, while preventing the bone from being bent by the hands of a human in the unlocked position.

As set forth in the preceding paragraph, the beam 22 in the bone plate 20 has one measure of stiffness in an unlocked position and a different measure of stiffness in an unlocked position. In general, the strength of any beam is a function of a beam stiffness factor associated with each mode of beam loading/deflection. The stiffness factor may be defined as the product of the modulus of elasticity E of the beam material times the moment of inertia I about the neutral axis in the direction of the beam deflection. Given a beam material, a comparison of the moments of inertia for the proposed and conventional reconstruction bars may help predict the usefulness of the proposed material as a flexible member 24 for the beam 22 in the disclosed bone plate 20. For example, if a one-millimeter square wire is used to form each flexible member 24, the sum of the individual bending moments of inertia about the neutral axis of the four beams in the vertical direction is about 0.33 mm$^4$. Using such wire for the beam described for FIGS. 12A and 12B, the bending moment of inertia of the beam 22 in the locked position shown in FIG. 12B would be about 5.33 mm$^4$, or 16 times the stiffness of the arrangement described for FIG. 12A. Since the beam 22 has a pair of spaced apart bundles of flexible members 24 (i.e., the coil 30 provides two beams 22 with each beam extending through the locking members 26), the overall bending moment of inertia in the vertical (up-and-down) direction (shown in FIG. 12B) is twice that of the single beam (i.e., 10.66 mm$^4$ rather than 5.33 mm$^4$). In the transverse (side-toside) direction, a pair of spaced-apart laminated beams as shown in FIG. 12B has an overall bending moment of inertia of about 333 mm$^4$.

FIGS. 13-16 show numerous views of an alternative embodiment of the bone fixation device shown in FIGS. 1-12. In the embodiment of FIGS. 13-16, the beam 22 comprises six flexible members 24 rather than the four flexible members shown in FIGS. 1-12. The six flexible members 24 in FIGS. 13-16 are formed from 0.50 mm wire wound in a coil 30 to provide a grouping having six layers of flexible members 24. The spacing between the centers of the screw holes 60 in each locking member 26 is typically about 16.7 mm. The screw holes are sized for receiving standard, 5 mm cortical bone screws.

Figure 18:
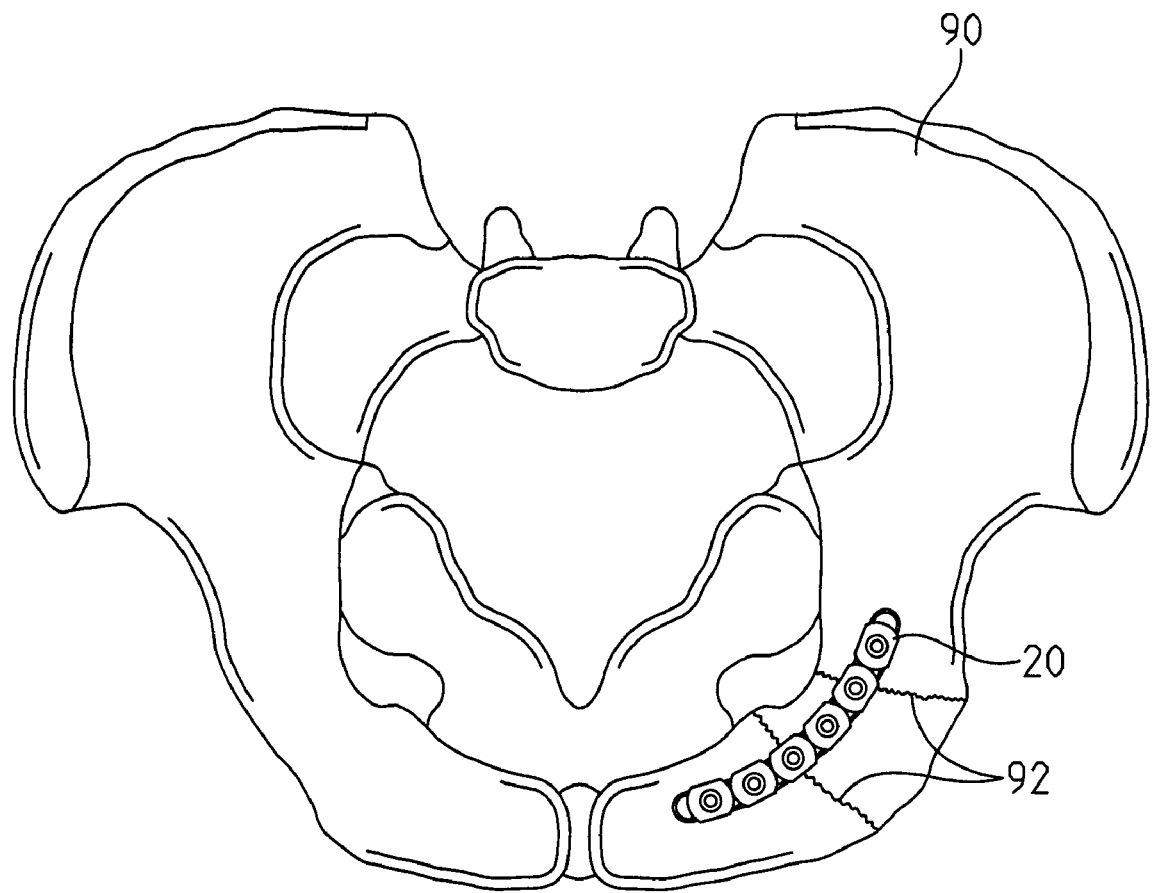
FIG. 18 shows an anterior view of a portion of a human pelvis, showing the bone fixation device of FIG. 1 attached to the pelvis.

In operation, the flexible bone fixation device 20 is configured for attachment to a fractured or otherwise damaged bone. FIG. 18 shows the bone fixation device 20 positioned upon a human pelvis 90. The bone fixation device 20 extends over the fractures 92 in the pelvis. When positioning the bone fixation device 20 upon the pelvis, the surgeon first clears the tissue from the fracture to expose the bone. Next, the surgeon places the bone fixation device 20 on the bone with the plurality of flexible members 24 in the unlocked relationship and the bone fixation device spanning across the fracture 92. The surgeon presses on the bone fixation device, applying bending forces to the appropriate locations on the bone fixation device such that the bone fixation device generally conforms to the contours of the bone and is curved or otherwise conformed to a desired shape. Accordingly, the bone fixation device may be bent in three dimensions (i.e., vertical bends, lateral bends, as well as twisting bends). Bending of the bone fixation device 20 may also be envisioned in relation to a curvilinear axis that extends along the length of the bone fixation device 20 generally parallel to the beam 22. Accordingly, the beam 22 may be bent laterally (side-to-side) relative to the curvilinear axis, vertically (up-and-down) relative to the curvilinear axis, or twisted about the curvilinear axis.

After the bone fixation device 20 is bent to the desired shape, the surgeon then starts the process of securing the bone fixation device to the bone. Starting at one end of the bone fixation device, the surgeon uses the holes 50 in the locking members 26 as a guide to drill a hole in the bone. The surgeon then inserts a bone screw through the hole and into the bone. When the bone screw is tightened in the locking member 26, the locking member compresses the plurality of flexible members together, placing the plurality of flexible members in a locked relationship at that location along the curvilinear axis of the bone fixation device 20. The surgeon follows this procedure to the opposite end of the bone fixation device until all of the locking members secure the plurality of flexible members in a locked relationship, and the bone screws are fixed to the bone. Alternatively, the surgeon may fully insert a bone screw in a hole in the middle of the bone fixation device 20 and proceed to fully insert the next bone screw in an adjacent hole in either direction, until all the screws are fully inserted. Furthermore, in some surgical applications, it may be desirable to partially insert all the bone screws into the holes of the fixation device 20, and then to tighten each screw starting from either end of the device 20, or the middle of the device 20. For each of the above-described procedures, it is generally desirable to position each locking member against the bone surface prior to fully tightening the bone screw through the locking member. However, there may be some surgical situations where the surgeon prefers to attach the fixation device to the bone surface with a gap between the bone surface and at least some of the locking members.

With the above described procedure, a bone fixation device is provided that is easily bent to match the contours of the bone surface. The forces required to bend the bone plate may be provided by the human hand. Because the bone fixation device is easily shaped, and no tools are required to bend the bone fixation device, the time needed to perform the surgical procedure installing a bone fixation device is reduced. In addition, because a single bone fixation device may be bent into numerous shapes, there is a reduced need to have bone fixation devices of various shapes on hand, and hospital inventories of bone fixation devices may be reduced.

Figure 17:
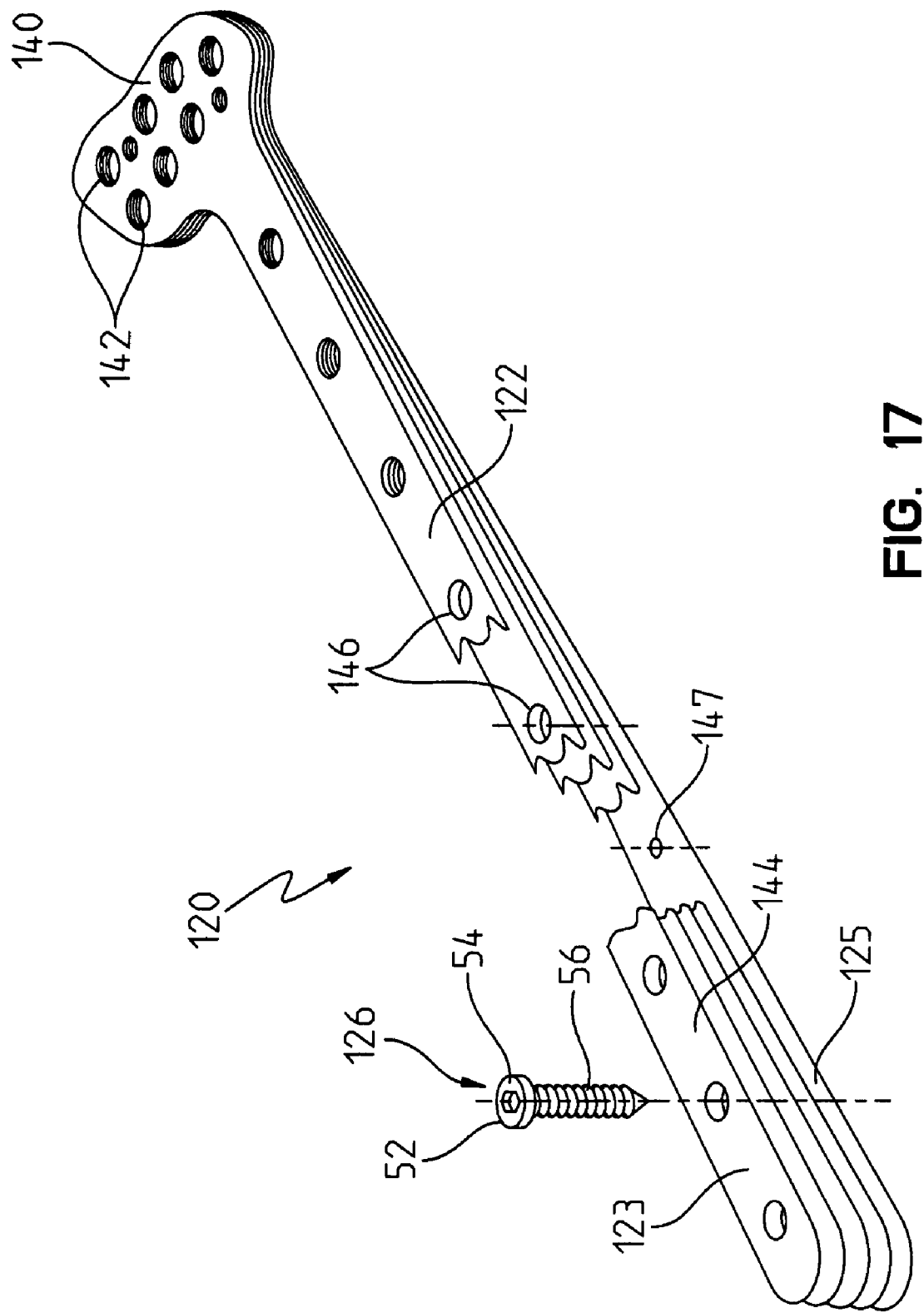
FIG. 17 shows a perspective view of an alternative embodiment of the flexible bone fixation device of FIG. 1.

FIG. 17 shows another alternative embodiment of a bone plate 120 that may be applied as a bone fixation device for fixation of various bones, such as the proximal humerus. As in the above-described embodiments, the bone fixation device 120 includes a load carrying structure formed from a plurality of flexible members 124. The flexible members 124 are provided as a plurality of elongated laminates formed from thin sheets of a biocompatible metal, polymer, fabric, paper, absorbable material, or other suitable material.

In the embodiment of FIG. 17, the bone fixation device 120 includes a head portion 140 and a stem portion 144. The laminates 124 may be partially joined near the head end, such as by welding, cementing, etc., in order to keep the laminates in general alignment. However, in other embodiments the laminates 124 may be initially separated from each other. The head portion 140 includes a plurality of holes 142 that extend through the laminates. Each of the plurality of holes 142 are configured to receive one of the locking members 126, such as, for example, a polyaxial locking screw 52, a non-locking screw, a guidance wire, a suture, or other locking member.

The stem portion 144 of each laminate 124 also includes a plurality of holes 146. The holes 146 in each laminate layer are aligned to allow a bone screw or other fixation device to pass through the aligned holes. The laminates 124 on the stem portion 144 may be initially provided with or without the stem holes 146.

If holes 146 are not initially provided in the stem portion 144, the surgeon may drill each hole through the laminates 124 and into the bone in a single step. However, before drilling any hole 146 the surgeon first presses the portion of the laminates that will receive the hole against the bone surface to properly bend the laminates into alignment with the bone. In this embodiment, the upper flexible member, such as laminate 123 in FIG. 17, may also include small pilot holes to guide the tip of the drill. The surgeon applies spaced-apart screws in this manner, proceeding from a location near the head of the plate, and moving towards the opposite end. After drilling each hole, the surgeon inserts a screw through the hole, thereby locking the laminates together at that location and attaching that portion of the plate to the bone.

Alternatively, if the holes 146 are initially provided in the stem portion 144, the holes 146 are spaced apart according to a pre-determined configuration. In this embodiment, the holes 146 in the bottom flexible member 124 that contacts the bone surface, such as hole 147 in laminate 125 shown in the cutaway portion of FIG. 17, may be sized for guiding the bone drill and for locking engagement with the thread of a cortical bone screw. The holes 146 in the other flexible members 124 above the bottom laminate 125 may be significantly larger than the major diameter of the bone screw thread. In one embodiment, the holes are successively larger in each laminate layer above the bottom laminate 125. In particular, the head of the bone screw will generally have a larger diameter than the smallest diameter of the larger holes on the upper laminate layer. This arrangement allows the flexible members to be bent while still allowing the pre-drilled holes 146 to remain in sufficient alignment to allow a bone screw to pass through the holes 146. Specifically, when the flexible members 124 are bent, the position of a hole 146 in the top laminate 123 will shift to a different extent than a hole in the bottom laminate 125. However, the holes 146 in the upper laminates are sufficiently larger than holes in the lower laminate 125 such that a passage remains through the holes that will accept a bone screw, despite the slightly shifted/offset position of the holes relative to one another. In this embodiment, the holes in the laminates 124 may be circular or elongated in the form of slots. In particular, elongated slots in the upper laminates are advantageous to ensure hole alignment following bending of the bone fixation device.

With pre-formed holes in the bone fixation device 120, the surgeon begins attaching the device 120 to the bone starting at the set of holes near the head 140 of the bone fixation device 120. The surgeon pushes the laminates 124 against the bone surface at that location and use the smaller hole 146 in the bottom laminate 125 to guide the bone drill. The surgeon may then immediately insert a bone screw through all the laminates at that location and tighten the screw, thereby locking the laminates together at that location. The surgeon may then proceed to the next hole location and repeat the procedure until all the screws are in place. As described above, the upper laminate holes provide significant clearance for the screw threads while the holes in the bottom laminate 125 are configured to engage the screw threads. Although the laminates may shift with respect to each other as the surgeon shapes the plurality of flexible members to conform to the bone contours, the differently sized holes still allow for passage of the bone screw. Once the bone screws are tightened, compressing the laminates 124 against the bone, the beam 122 is in the rigid/locked condition and configured for fixation of the bone fracture.

The laminates 124 shown in FIG. 17 may be made from any one of numerous materials including metals and polymers, and may be adhered together, at least provisionally until screws are inserted, with a biocompatible bonding agent such as cyanoacrylate cement or bone cement. The laminates may also be formed form a metallic mesh material which provides numerous holes in each layer. By using such a mesh material, it is not necessary to drill holes into the laminates, and the holes in the mesh may provide for passage of the bone screw through the laminates.

In other embodiments, the laminates 124 of the bone fixation device 120 of FIG. 17 may be formed from different materials that provide additional features and benefits. For example, the bottom laminate 125 may be made of a resilient material such as silicone rubber to provide a conformable interface against the bone surface, thereby helping to preserve blood flow in the periosteum. Alternatively, the bottom laminate 125 may be formed from an absorbent material such as a sterile cotton fabric containing a therapeutic agent such as an antimicrobial to help prevent infection of tissues at the wound site. Intermediate laminates may be made of materials design to augment the flexibility, hardness, fatigue resistance, and other mechanical properties, thereby forming a composite flexible bone plate with improved properties.

In one embodiment, the laminates 124 of FIG. 17 may be cut to length during the surgical procedure. For example, the flexible bone plate 120 shown in FIG. 17 may be provided with an extra long stem 144 to accommodate an extremely large patient. The surgeon may then use surgical shears to cut each laminate 124 to the desired length. In this way the surgeon may also stair step or taper the end of the stem to more nearly resemble the formation of natural callus over the fracture. In one embodiment, a roll of laminate may be provided such that the surgeon may cut a desired number of flexible elements from the roll, align them in a vertically layered configuration, and attach them to the bone. The rolled laminate may include an adhesive for provisional placement of the layers until the screws are tightened against the bone. The laminates may also be provided in sheet form rather than strips. Many other variations of laminates, flexible members, plates and related methods of using such members may be envisioned by those skilled in the art.

Figure 19:
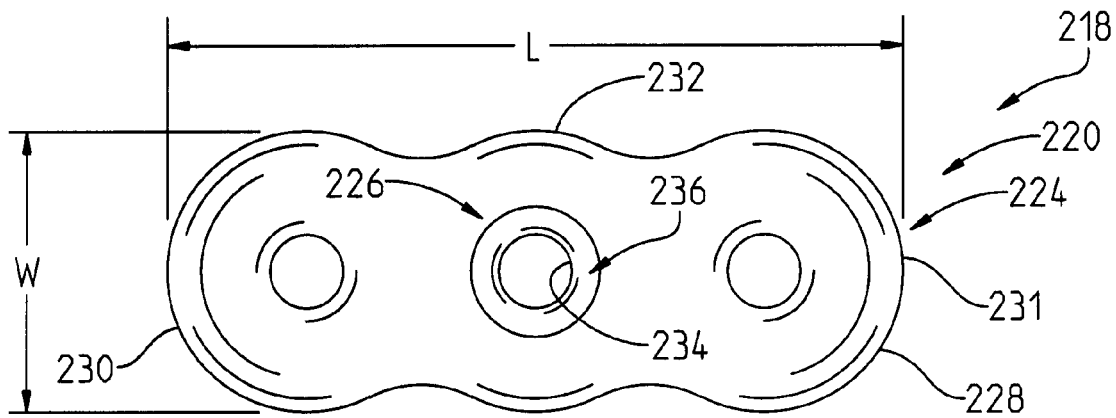
FIG. 19 shows a top view of another alternate embodiment of the flexible bone fixation device.

Referring now to FIG. 19, another embodiment of a bone fixation device is shown as bone fixation device 220. The bone fixation device 220 includes a first construct 218 including a plurality of first flexible members 224. The bone fixation device 220 further includes a first locking member that serves primarily as a retaining member or a first assembly member 226 for assisting in retaining or assembling the flexible members 224 against each other. The first assembly member 226 may include cortical or cancellous bone threads 233 that engage bone 2. The assembly member 226 may be in the form of a polyaxial locking screw, a non-locking screw, or other locking member and may be cannulated. An example of a polyaxial locking screw is more fully described in U.S. Pat. No. 5,954,722 to Bono the disclosure of which is herein incorporated by reference in its entirety. The flexible members 224 as shown for simplicity each has a similar shape and has a periphery 228 defining a length L and a width W. As shown in FIG. 19, the periphery 228 may have a generally arcuate shape with edges that are curved or chamfered to avoid damage to bone or soft tissue. The periphery may include generally circular end portions 230 and 231 and a generally cylindrical central portion 232. The flexible member may have any alternate shape as appropriate.

Each of the flexible members 224 may have an interior wall 234 which defines an opening 236 through the flexible member 224. The opening 236 may serve to receive the first assembly member 226.

Figure 20:
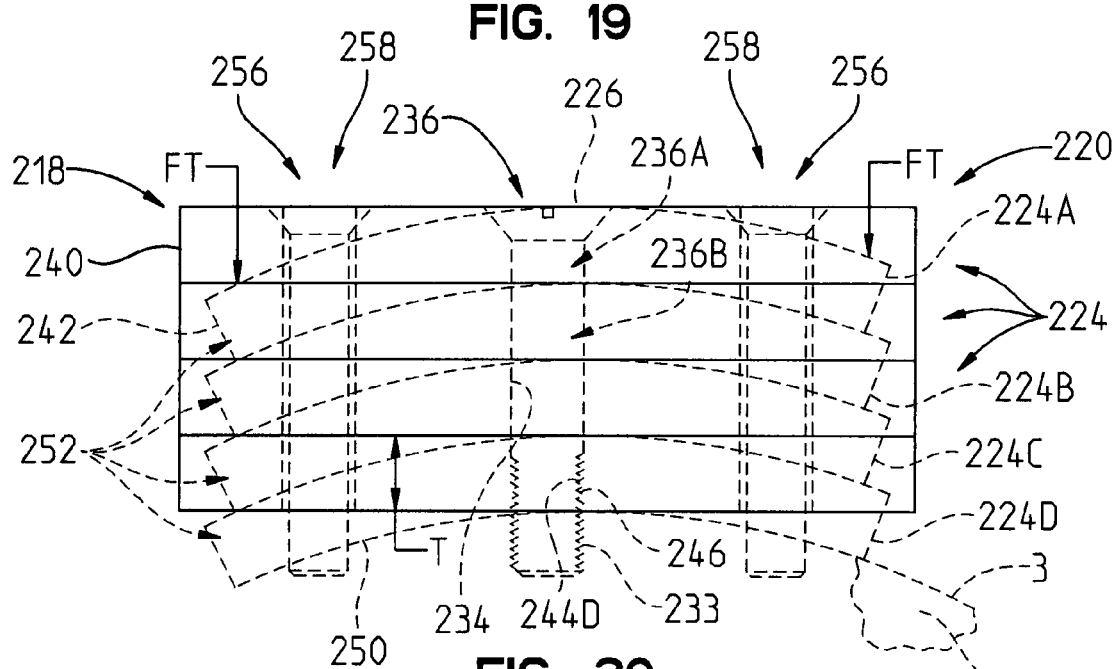
FIG. 20 shows a side view of the flexible bone fixation device of FIG. 19 in the unlocked relationship.
Figure 21:
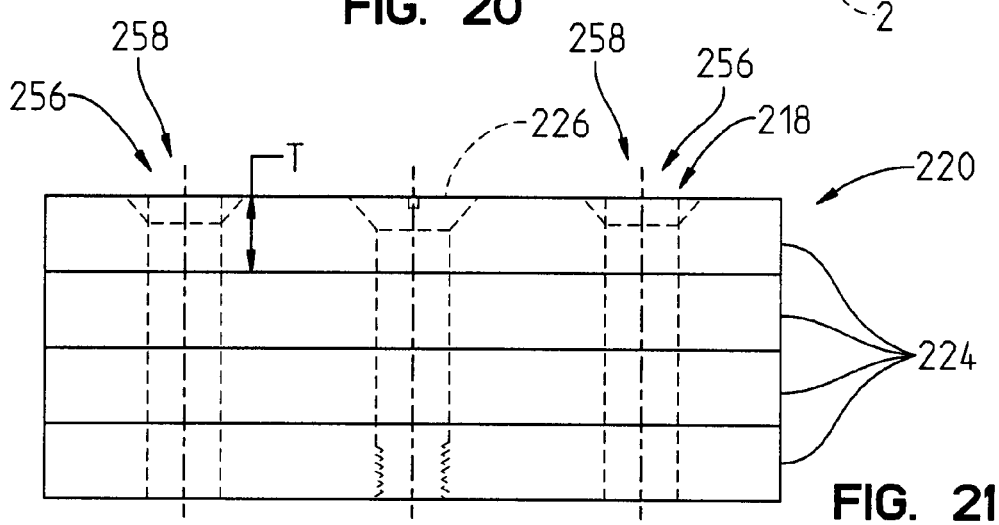
FIG. 21 shows a side view of the flexible bone fixation device of FIG. 19 in the locked relationship.

Referring now to FIG. 20, the plurality of first flexible members 224, when exposed to a first threshold force FT, deflect or bend from first position 240 as shown in solid to second position 242 as shown in phantom. When first assembly member 226 is advanced against the flexible members 224 to compress the plurality of first flexible members 224 together it should be appreciated that some increase in the rigidity of the plurality of first flexible members 224 occurs. However, the increase in rigidity occurs mostly close to the assembly member 226. Further from the assembly member 226, the plurality of first flexible members 224 are still quite flexible. To provide a rigid construct to the plurality of first flexible members 224 against the bone 2 and into a locked relationship as shown in FIG. 21 and in order for the members 224 to stay curved against the bone 2, typically the opposing ends of the members 224 are clamped. One method of clamping the opposing ends is by inserting and tightening two bone screws 256 into openings 258 while members 224 are held in the curved configuration. The two bone screws 256 serve as additional locking members. When the two bone screws 256 and the assembly member 226 are secured to the plurality of first flexible members 224 and when the first threshold FT is applied to the first construct 218, the first threshold force FT is insufficient to deflect or bend the plurality of first flexible members 224.

Referring again to FIG. 20, the plurality of first flexible members 224 may have any plural numbers of flexible members. For example two, three, four, or more first flexible members 224 may be utilized in the construct 218. The construct 218 may include four first flexible members, namely first first flexible member 224A, second first flexible member 224B, third first flexible member 224C, and fourth first flexible member 224D.

For simplicity, each of the first flexible members, 224A, 224B, 224C, and 224D may have identical dimensions and may include a common thickness T. It should be appreciated that the thickness T of the first flexible members is typically chosen to provide for flexibility of the flexible members 224 when not locked with the assembly member 226. For example, if the flexible member 224 is made of a metal, for example a titanium alloy, a cobalt chromium alloy or a stainless steel alloy, the thickness T may be from, for example, 0.30 to 1.80 millimeters.

The first flexible members 224 are joined together by first assembly member 226 to form first construct 218. The first flexible member opening 236 receives the first assembly member 226. For example, the first of the first flexible members 224A includes an opening 236A, while the second 224B of the first flexible members includes an opening 236B for receiving the first assembly member 226, etc.

The bottom or fourth of the first flexible members 224D may include internal threads 244D for cooperation with external threads 246 on the first assembly member 226. The internal threads 224D and the external threads 246 connect the flexible members 284 into a locked relationship close to the opening 236.

Referring again to FIG. 20, the construct 218 may be fitted to any irregularly shaped bone 2. For example, the construct 218 may be suited for use with bone 2 having a concave periphery 3. The bottom surface 250 of the lower plate 224D may closely conform to the periphery 3 of the bone 2 when in an unlocked relationship as shown as dashed line 252. Upon locking the flexible members 224 with two bone screws 256, the bottom surface 250 maintains a mating relationship with periphery 3 of bone 2. When the bone 2 has a convex periphery 254 as shown in phantom, the bone screws 256 positioned in openings 258 of flexible members 224 maintain the shape of the flexible members 224 and lock the flexible members 224 in the position 242 shown in phantom.

While the fixation device of the present disclosure may be in the form of fixation device 220 of FIGS. 19-21 including only the plurality of first flexible members 224, the bone fixation device may alternatively be in the form of a fixation device that includes a second construct in addition to a first construct. Referring now to FIGS. 22-29 another embodiment of the present disclosure is shown as fixation device 320. The fixation device 320 includes a second construct 348 in addition to a first construct 318. The first construct 318 and the second construct 348 together provide a larger more complex device to accommodate larger fractures and irregular bone shapes. The first construct 318 includes a plurality of first flexible members 324. The second construct 348, like the first construct 318, includes a plurality of second flexible members 338. The plurality of first flexible members 324 and the plurality of second flexible members 338 may have any suitable size and shape and may have a rectangular, oval or figure-8 shape.

Figure 22:
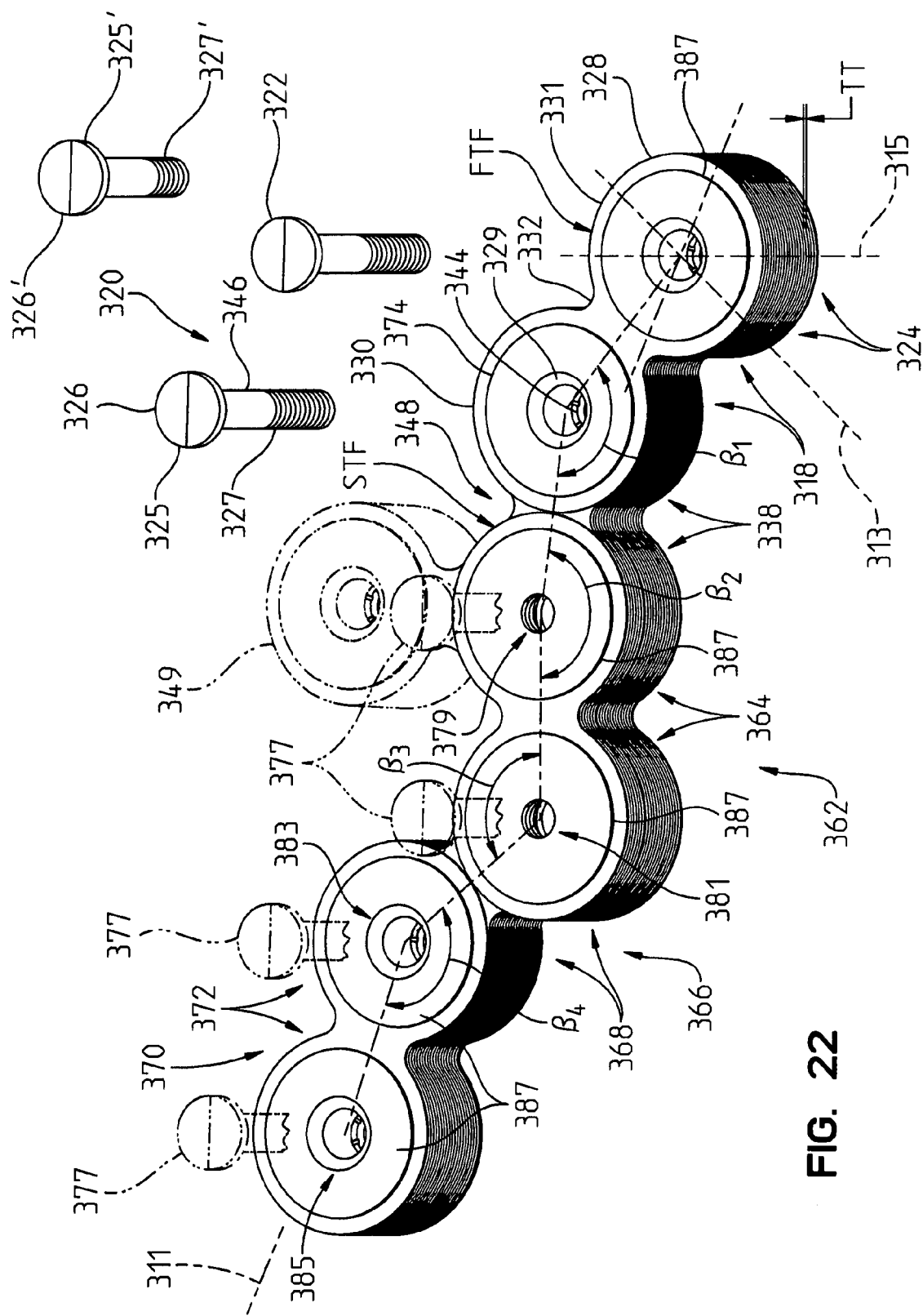
FIG. 22 shows a perspective view of another alternate embodiment of the flexible bone fixation device.

The bone fixation device 320 as shown in FIG. 22 includes the first construct 318 with a plurality of first flexible members 324 and a first locking member 326 configured to compress the plurality of first flexible members 324 together and into a locked relationship. The first locking member 326 includes a head 325 that seats into chamfer 329 of device 320 and external threads 346 which engage internal threads 344 of device 320. When tightened, the locking member 326 draws the plurality of first flexible members 324 into a locked arrangement. It should be appreciated that the first locking member may alternatively or in addition include bone threads 327 that engage bone to secure the device 320 to bone. If the external threads are absent as shown in locking member 326' (shown in phantom), bone threads 327' engage bone and with head 325' draw the plurality of first flexible members 324 into a locked arrangement.

The first locking member 326 may be in the form of a polyaxial locking screw or a non-locking screw. A second locking member 322, similar to the first locking member 326, may also be used to secure the plurality of first flexible members 324 to each other. The first flexible members 324 are selected such that the plurality of first flexible members 324 are configured to bend when a first threshold force FTF is applied to the first construct 318 and the plurality of first flexible members 324. The first locking member 326 is configured to compress the plurality of first flexible members 324 together into a locking relationship. The first threshold force FTF, when applied to the first construct 318 in the locked relationship is insufficient to bend the plurality of first flexible members 324.

The bone fixation device 320 may include additional constructs in addition to the first construct 318. The additional constructs may provide for a bone fixation device 320 that has a variable shape. The shape may be elongate and may be that of a ribbon. Such a bone fixation device is well suited for long bones and for areas of the pelvis where long complex fractures may occur. For use in the pelvis and other bones that have a complex non-planar periphery, the additional constructs may be configured in any conceivable shape in any of three dimensions. Orthogonal x axis 311, orthogonal y axis 313, and orthogonal z axis 315 are defined such that the longitudinal axis of device 320 is the x axis 311, the z axis 315 is perpendicular to the top or bottom surface of device 320 (into the bone) and the y axis 313 is parallel to the top or bottom surface of device 320, the device 320 may be bent in the x-z plane to conform to the topography of the bone surface. Further, the constructs may be pivoted with respect to each other (like a bicycle chain) to be reconfigured in the x-y plane. The bicycle chain construction may be useful, for example, for configuring the device to wrap around an acetabular fracture. Also, the device 320 may be slightly twisted about the x axis. This is especially useful for following a flat surface of the diaphysis of a long bone as the surface wraps around the longitudinal axis of the bone.

For example and as shown in FIG. 22, the bone fixation device 320 may include the second construct 348 including the plurality of second flexible members 338. The bone fixation device 320 may be configured such that the first flexible members 324 and the second flexible members 338 are interwoven or positioned in an overlapping alternating arrangement.

The second flexible members 338 are configured to bend when a second threshold force STF is applied to the second construct 348 and the plurality of second flexible members 338 are in an unlocked relationship. Further, similar to the first construct 318, the second construct 348 utilizes the first locking member 326 to compress the plurality of flexible members 338 together and into a locked relationship. The second threshold force STF applied to the second construct 348 is insufficient to bend the plurality of second flexible members 338 when in the locked relationship. The first flexible members 324 and the second flexible members 338 are in the form of plates having a thickness TT. The number of flexible members or plates and the thickness of each member or plate are chosen to provide sufficient strength in the locked relationship to adequately support a fractured bone and sufficient flexibility in the unlocked relationship to conform to the contour of the bone. For example the plates may have a thickness of 0.050 to 1.300 millimeters and total number of plates may be from three to thirty plates. For example, for a construct having twenty plates with each plate having a plate thickness of 0.125 millimeters, the construct has a thickness of 2.50 millimeters. When two constructs are joined together as shown in FIG. 23, and each construct has 20 flexible members, a total of 40 flexible members are stacked together with an overall height of 5.00 millimeters.

Figure 23:
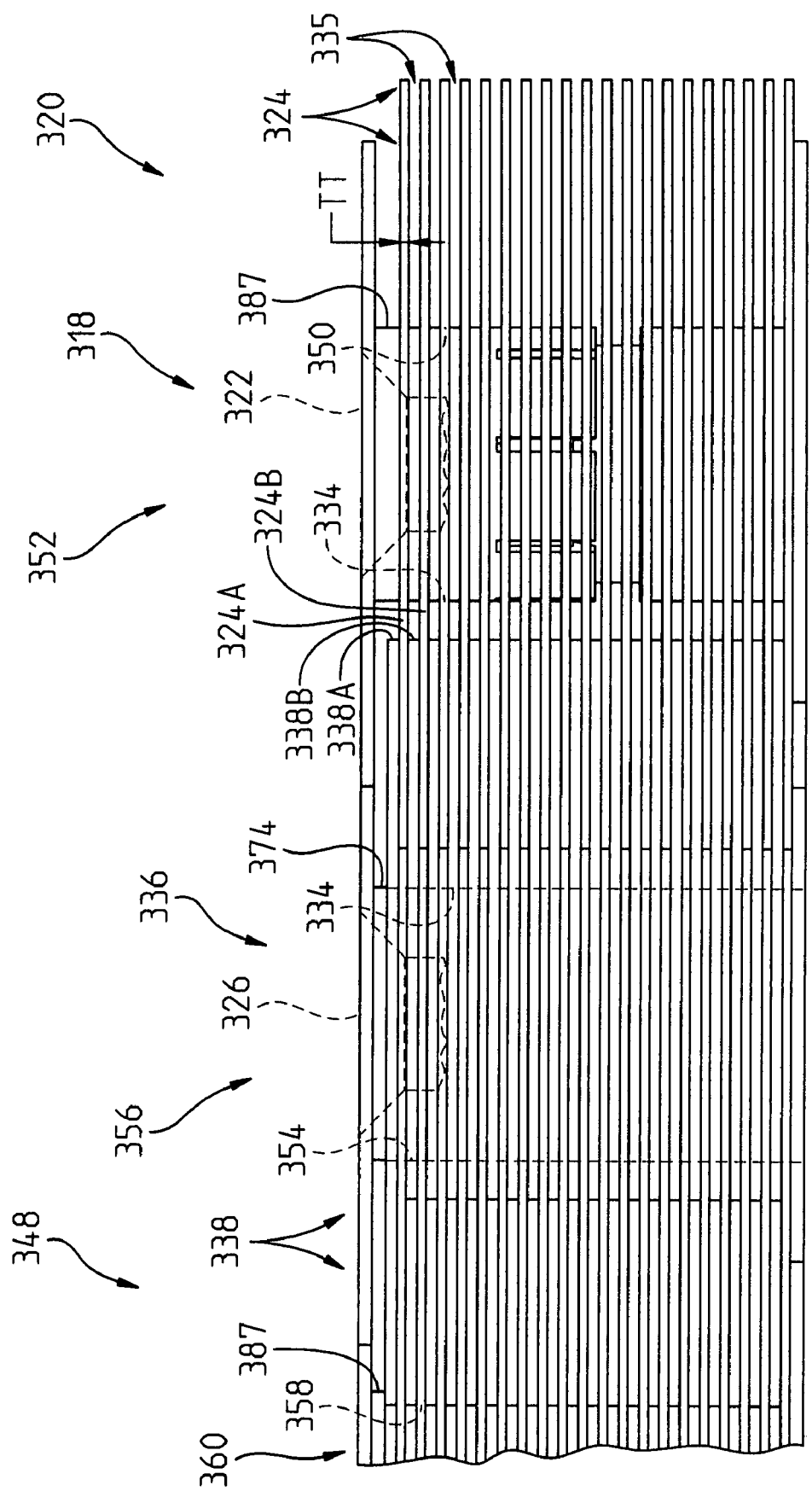
FIG. 23 shows a partial side view of the flexible bone fixation device of FIG. 22.

Referring now to FIG. 23, the first flexible members 324 and the second flexible members 338 are alternately positioned between each other. For example, the second member 338B of the second flexible members 338 is placed between the first member 324A of the first flexible members 324 and the second member 324B of the first flexible members 324. Similarly, the first member 324A of the first flexible members 324 is placed between the first member 338A of the second flexible members 338 and the second member 338B of the second flexible members 338.

Each of the first flexible members 324 includes a first internal wall 334. Each of the first internal walls 334 defines a first member first opening 336. Similarly, each of the plurality of first flexible members 324 includes a second internal wall 350. Each of the second internal walls 350 defines a first member second opening 352.

Further, each of the plurality of second flexible members 338 include a first internal wall 354. Each of the first internal walls 354 defines a second member first opening 356. The first locking member 326 is configured to cooperate with each of the first member first openings 336 and the second member first openings 356. Similarly, the plurality of second flexible members 338 of the second construct 348 each further include a second internal wall 358 defining a second opening 360 of the second set of flexible members 338.

As shown in FIG. 23, a gap or space 335 is formed between adjacent first flexible members 324 around the first member second openings 352. It should be appreciated that flexible members or plates (not shown) may be fitted into the gaps 335. The plates may each have a cylindrical shape and have an opening for receiving the second locking member 322. The plates may provide for a more rigid construct around the first member second openings 352. Similar plates may be fitted into gaps around the opposed end of the bone fixation device 320.

It should be appreciated that any number of constructs may be utilized in the bone fixation device of the present disclosure. Each of the constructs may extend from the prior construct providing a ribbon of unlimited length and having endless choices of shapes. For example and as shown in FIG. 22, the bone fixation device 320 further includes a third construct 362 including a plurality of third flexible members 364. The third construct 362 extends from second construct 348. The bone fixation device 320 includes a fourth construct 366 including a plurality of fourth flexible members 368. The fourth construct 366 extends from the third construct 362. Further and as shown in FIG. 22, the bone fixation device 320 includes a fifth construct 370 extending from the fourth construct 366. The fifth construct 370 includes a plurality of fifth flexible members 372.

The bone fixation device 320 may include additional locking members 377, similar to locking members 322 and 326 to hold the flexible members of the second construct 348, the third construct 362, the fourth construct 366, and the fifth construct 370 together in a rigid construct. One of the additional locking members 377 may fit into opening 379 of the second construct 348 and the third construct 362. Another of the additional locking members 377 may fit into opening 381 of the third construct 362 and the fourth construct 366. Yet another of the additional locking members 377 may fit into opening 383 of the fourth construct 366 and the fifth construct 370. Another of the additional locking members 377 may fit into second opening 385 of the fifth construct 370.

While each of the constructs may extend from each other linearly or along a common centerline, other shapes or configurations may be desired. For example and as shown in FIG. 22, the second construct 348 extends at angle $\beta_1$ with respect to first construct 318. Similarly the third construct 362 extends at an angle $\beta_2$ from second construct 348. Similarly, the fourth construct 366 extends at an angle $\beta_3$ from third construct 362. Further, fifth construct 370 extends at an angle $\beta_4$ from fourth construct 366. It should be appreciated that angles $\beta_1$ to $\beta_4$ may be any angles to provide whatever shape of bone fixation device preferred for a particular patient. It should also be appreciated that constructs such as construct 349 as shown in phantom may extend from any construct within the construct chain, providing for more complex shapes of bone fixation devices. The overall stack up height of the pivot joint at construct 349 will be greater than the stack height of the other pivot joints, but that may be acceptable. Additional constructs (not shown) may extend from construct 349 or any other construct. The flexible members of the construct 349 may be interwoven with the flexible members of the constructs 348 and 362.

Figure 22A:
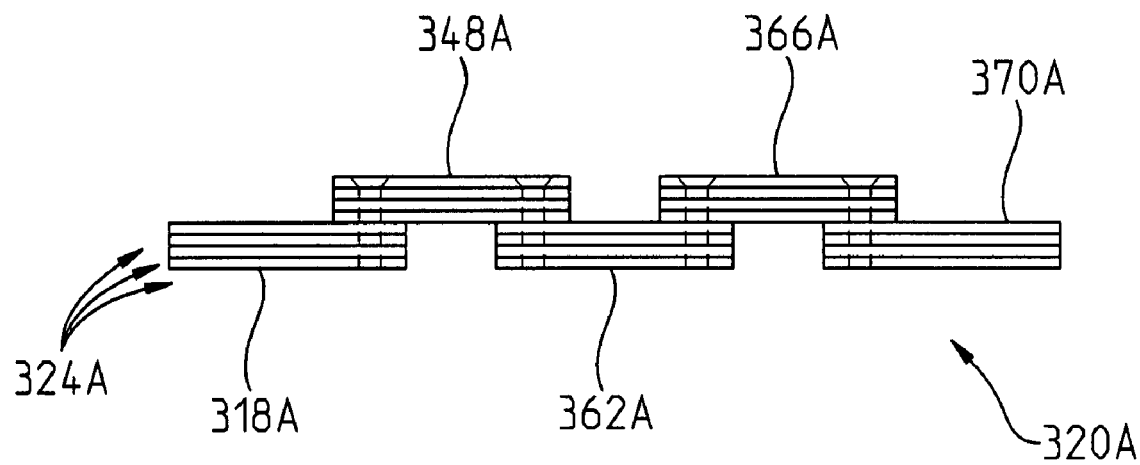
FIG. 22A shows a plan view of another alternate embodiment of the flexible bone fixation device.

It should be appreciated that the flexible members of adjacent constructs do not necessarily need to be alternately interwoven. For example and referring to FIG. 22A, a device 320A includes flexible members 324A. The flexible members 324A form a second construct 348A that is stacked on top of the flexible members 324A of first construct 318A and on top of the flexible members 324A of third construct 362A. Adjacent constructs are placed above or under each other. For example, odd constructs 318A, 362A, and 370A may be below adjacent constructs and even constructs 348A and 366A may be above adjacent constructs, with only the odd constructs 318A, 362A, and 370A contacting bone.

Figure 22B:
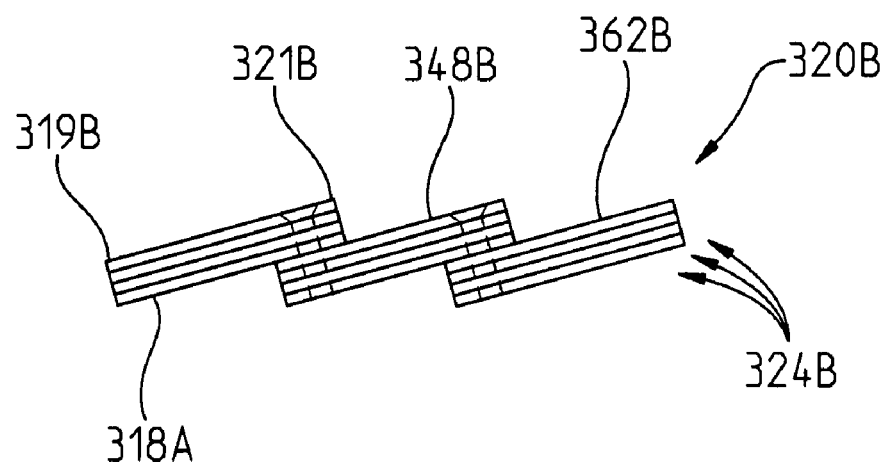
FIG. 22B shows a plan view of another alternate embodiment of the flexible bone fixation device.

Alternatively and referring to FIG. 22B, a device 320B includes flexible members 324B in which adjacent first and second constructs 318B and 348B, respectively have a construction similar to a fallen line of dominos, with first end 319B of first construct 318B being in contact with bone and the second end 321B of first construct 318B being spaced from the bone.

The first locking member 326 may be configured in any fashion to compress the first flexible members 324. For example, the first locking member may be threadably engaged with the bottom flexible members, similar to the fixation device 220. Partially tightened locking elements may then be used to constrain the plurality of flexible plates for positioning the device against bone prior to locking the device. The partially tightened locking members may then be fully tightened to provide for the locking relationship.

Alternatively, a separate feature may be desired to contain the flexible members in an unconstrained relationship to position and align the various constructs of the bone fixation device in proper position along the bone of a patient. It should be appreciated that a variety of component designs may be used for the retainer to contain the plurality of flexible members in an assembled relationship in which the flexible members are not rigidly locked against each other. For example the retainer may be in the form of a threaded fastener, a rivet, or a pair of components that are welded or interference fitted together to provide a constraint.

As shown in FIG. 22, the bone fixation device 320 includes separate retainers such as first retainer 374 to retain the flexible members in an unlocked relationship while the locking members such as first locking member 326 may be separately used to lock the flexible members rigidly together. The retainers contain the flexible members while the bone fixation device is aligned to the desired position along the bone prior to locking the plates. Additional retainers 387 are utilized to receive the second locking member 322 as well as each of the additional locking members 377. The additional retainers 387 are similar to and for simplicity and as shown identical to the first retainer 374.

Figure 24:
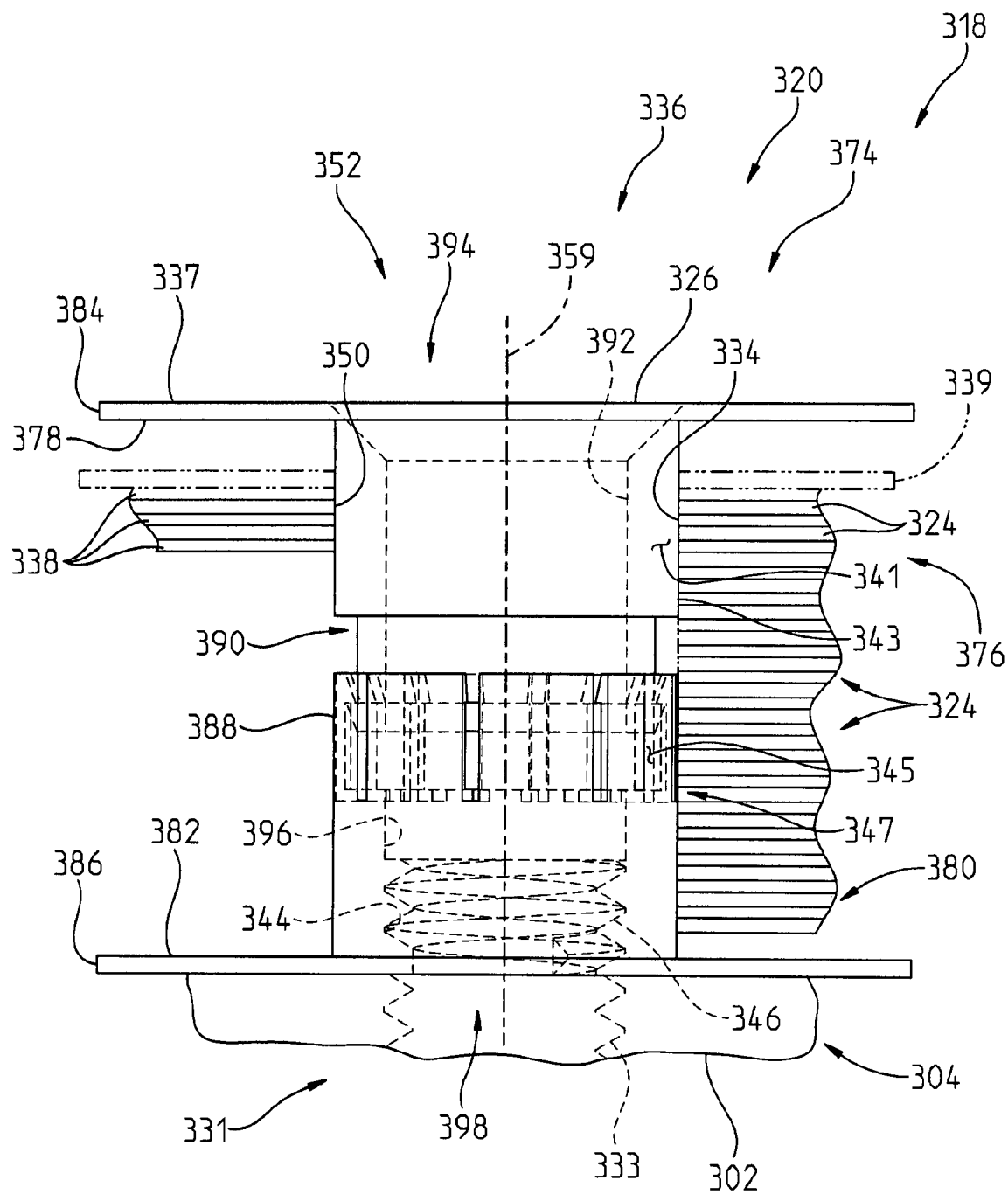
FIG. 24 shows a side view of a locking member, partially in cross section, in position in the flexible bone fixation device of FIG. 22.

Referring now to FIG. 24, the first retainer 374 is shown in greater detail. The retainer 374 includes a first retaining portion 376 and a second retaining portion 380. The first retaining portion 376 has a surface 378 configured for cooperation with one of the plurality of first flexible members 324 or one of the plurality of second flexible members 338. The second retaining portion 380 has a surface 382 that cooperates with an opposed one of the plurality of first flexible members 324 or one of the plurality of second flexible members 338. The plurality of first flexible members 324 and the plurality of second flexible members 338 are positioned between the surface 378 of the first retaining portion 376 and the surface 382 of the second retaining portion 380. The first retaining portion 376 as shown in FIG. 24 includes an upper plate 384. The upper plate 384 includes the surface 378. The second retaining portion 380 includes a lower plate 386. The lower plate 386 includes the surface 382 of the second retaining portion 380.

It should be appreciated that the upper plate 384 and the lower plate 386 may have a size and shape matching the plurality of first flexible members 324 or the plurality of second flexible members 338. Such plates typically include dual upper or dual lower retaining portions. Plates with dual upper retaining portions are typically alternately positioned next to dual lower retaining portions. As shown in FIGS. 22-29, however, the upper plate 384 of the first retaining portion 376 and the lower plate 386 of the second retaining portion 380 have a generally cylindrical or disc shape.

The first retaining portion 376 and the second retaining portion 380 may be integral with each other or may be separate components. As shown in FIG. 24 the first retaining portion 376 and the second retaining portion 380 are separate components and are removable from each other such that the plurality of first flexible members 324 and the plurality of second flexible members 338 may be easily assembled between the retaining portions 376 and 380. The first retaining portion 376 and the second retaining portion 380 may be interference fitted, threadably secured, or interlocked to each other. For example and as shown in FIG. 24, the first retaining portion 376 is snap fitted to the second retaining portion 380 by a plurality of spaced apart tabs 388 matingly fitted to groove 390 formed in first retaining portion 376 of the retainer 374.

It should be appreciated that a solitary tab 388 or a tab extending completely around the second retaining portion 380 may be utilized. Further, the groove 390 may include a separate recess for receiving each of the tabs 388. Further it should be appreciated that various other interlocks may be used that permit axial movement of the second retaining portion 380 with the first retaining portion 376 of the first retainer 374. It should be appreciated that the first retaining portion 376 and the second retaining portion 380 may be made of any suitable durable material and be made of, for example, a metal or a polymer that is compatible with the human anatomy.

As shown in FIG. 24 the first retaining portion 376 may include an internal wall 392 defining a first portion opening 394 in the first retaining portion 376. Similarly, the second retaining portion includes an internal wall 396 defining a second portion opening 398 in the second retaining portion 388. The first locking member 326 may include a bone fastener portion 331 sized for passage through the first portion opening 394 and the second portion opening 398. The bone fastener portion 331 of first locking member 326 may include bone threads 333 adapted for cooperation with bone 302 of patient 304. The bone threads 333 may be cortical threads or cancellous threads.

As shown in FIG. 24, the bone fastener 326 may include external locking threads 346 matingly fitted to internal threads 344 formed on second portion 380 of the first retainer 374. The first retaining portion 376 and the second retaining portion 380 are typically movable along center line 359 of the retainer 374 to provide for a locked relationship and an unlocked relationship. The plate contact surface 382 of the lower plate 386 is positioned with respect to the plate contact surface 378 of the upper plate 384 in first position 337 as shown in solid. In the first position 337, the first flexible members 324 and the second flexible members 338 are in an unlocked relationship. In a second position 339 as shown in phantom, the first flexible members 324 and the second flexible members 338 are in a locked relationship. To provide the unlocked relationship, the distance between surfaces 378 and 382 in first position 337 is greater than the sum of the thicknesses of the first flexible members 324 and the second flexible members 338.

As shown in FIG. 24, each of the plurality of first flexible members 324 includes an internal wall 334 defining first opening 336 and each of the plurality of second flexible members 338 includes an internal wall 350 defining a first opening 352 through the plurality of second flexible members 338. It should be appreciated that the openings 336 of the first flexible members 324 and the openings 352 of the second flexible members 338 are sized to receive periphery 341 of hub 343 of the first retaining portion 376 as well as to receive periphery 345 of hub 347 of the second retaining portion 380.

Figure 25:
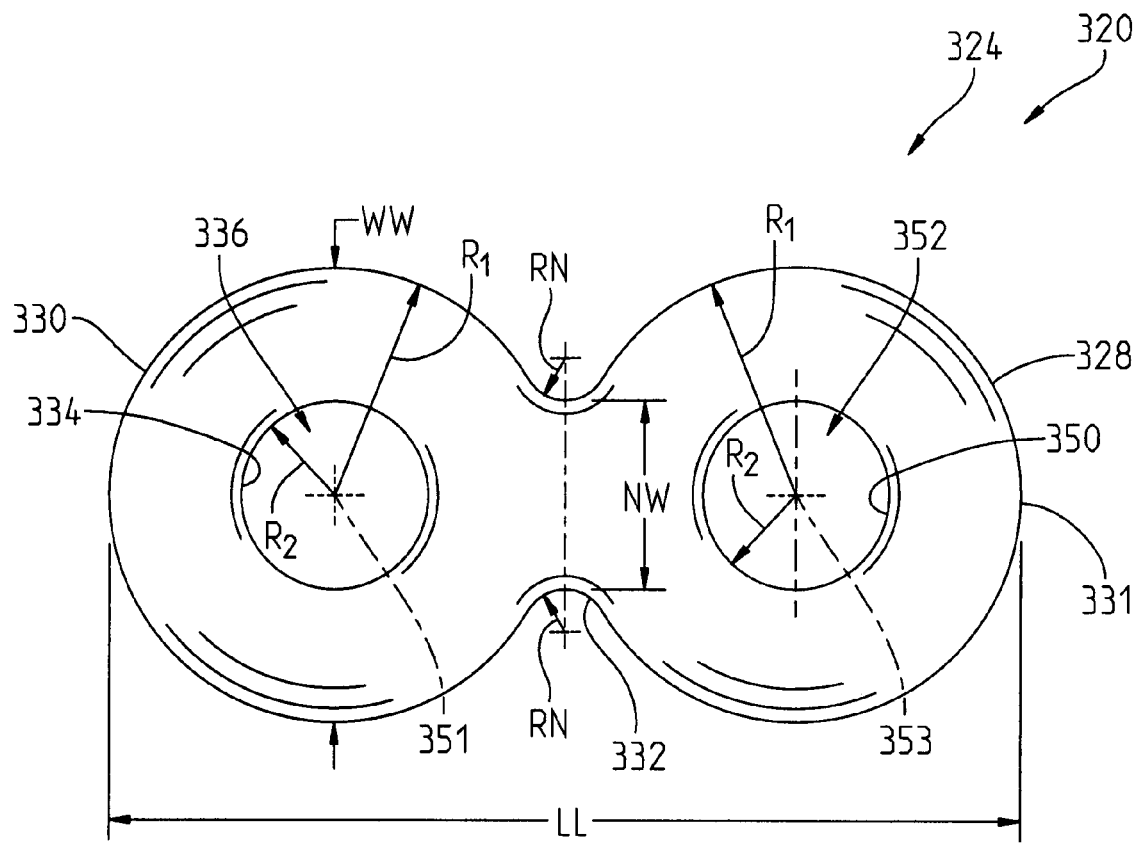
FIG. 25 shows a top view of the flexible member of the flexible bone fixation device of FIG. 22.
Figure 26:
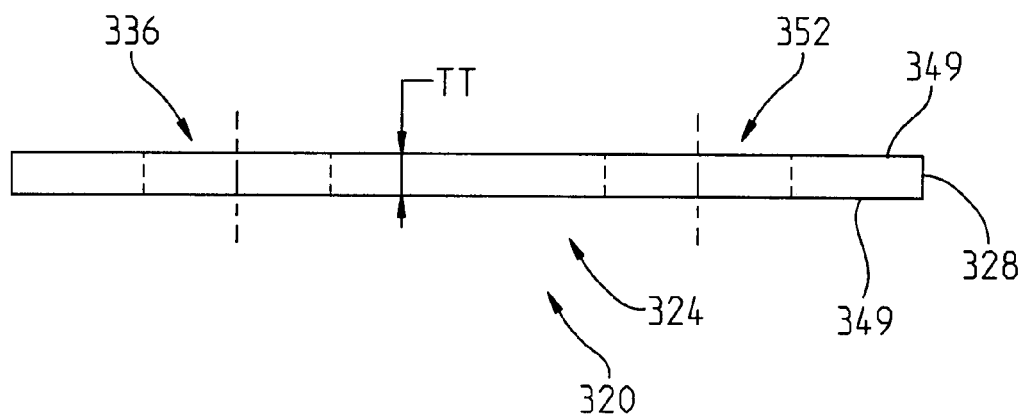
FIG. 26 shows a side view of the flexible member of FIG. 25.

Referring now to FIGS. 25 and 26, one of the plurality of first flexible members 324 is shown. The flexible member 324 includes a periphery 328. The flexible member 324 for simplicity has a uniform thickness TT such that flexible members 324 may be positioned against each other to form the plurality of flexible members 324. It should be appreciated that recesses or cavities may be formed on the opposed faces 349 of the flexible members 324.

Figure 8:
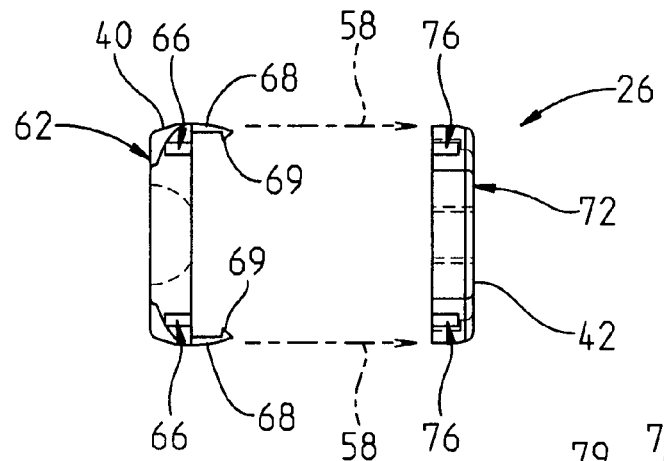
FIG. 8 shows a lateral side view of a top half and a bottom half of one of the plurality of locking members of FIG. 1 in a separated position.
Figure 9A:
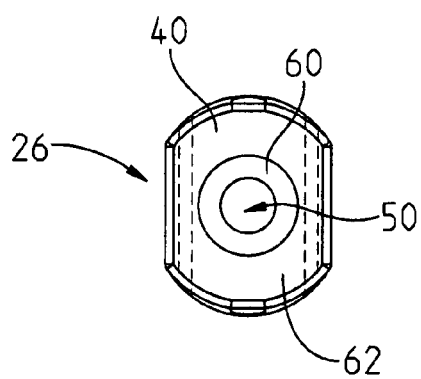
FIG. 9A shows a top view of the top half of the locking member of FIG. 8.
Figure 10A:
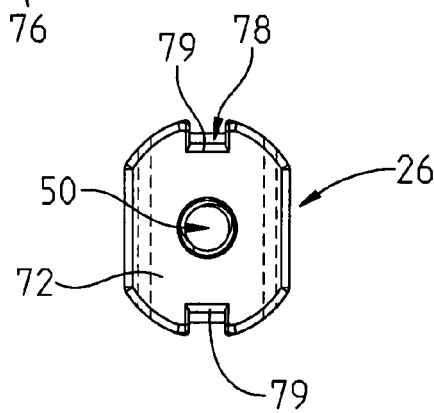
FIG. 10A shows a top view of the bottom half of the locking member of FIG. 8.
Figure 9B:
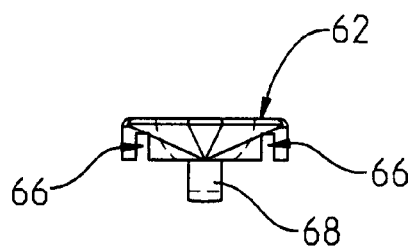
FIG. 9B shows an end side view of the top half of the locking member of FIG. 8.
Figure 10B:
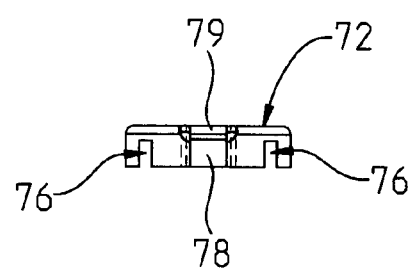
FIG. 10B shows an end side view of the bottom half of the locking member of FIG. 8.

The periphery 328 of the flexible member 324 may have any suitable shape and for simplicity may have a figure-8 shape with edges that are curved or chamfered to avoid damage to bone or soft tissue. The flexible member 324 has generally cylindrical first and second ends 330 and 331, respectively, connected to each other at neck 332. The periphery 328 of the ends 330 and 331 of the flexible member 324 is defined by radius R1 extending from first end center line 351 and second end center line 353, respectively. The flexible member 324 may be further defined by a neck width NW of the neck 332. The neck 332 may include radii RN to reduce stress risers in the flexible member 394. It should be appreciated that periphery 328 of neck 332 may alternatively have an oval or other shape. The flexible member 324 further includes the first opening 336 and the second opening 352. The openings 336 and 352 are defined by radii R2 extending respectively from center lines 351 and 353, respectively. These openings are larger in diameter than the diameter of the retainer inserted into them so that it is possible to flex the constructs in the z direction. The openings alternately may be slots rather than circularly shaped. The diametral clearance between the retainer outer diameter and the opening diameter is typically approximately in the range of 0.5-1.5 mm for the current embodiment.

Figure 27:
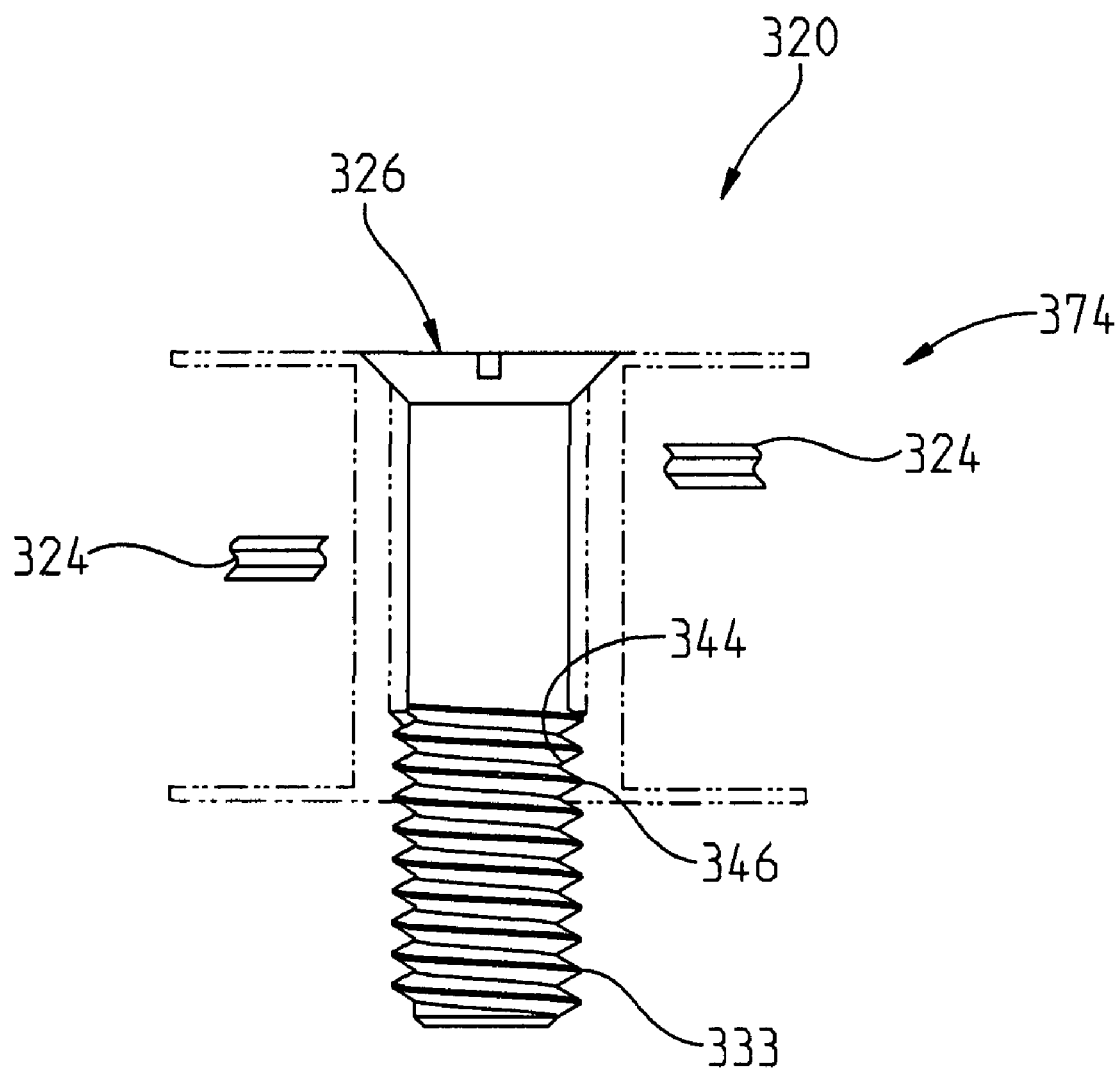
FIG. 27 shows a plain view of a fastener for use with the flexible bone fixation device of FIG. 22.

Referring now to FIG. 27, the first locking member 326 is shown in position in first retainer 374 of the bone fixation device 320. The first locking member 326 includes the external locking threads 346 for locking the plurality of first flexible members 324. The first locking member 326 further includes bone threads 333 which may be cortical or cancellous threads. The bone threads 333 have a similar pitch and diameter as the external locking threads 346 of the first locking member 326 such that the bone threads 333 of the first locking member 326 may be threadably assembled into the first retainer 374. It should be appreciated that the external locking threads 346 may be multiple lead threads to provide the added strength to lock the plurality of the first flexible members 324 together.

Figure 28:
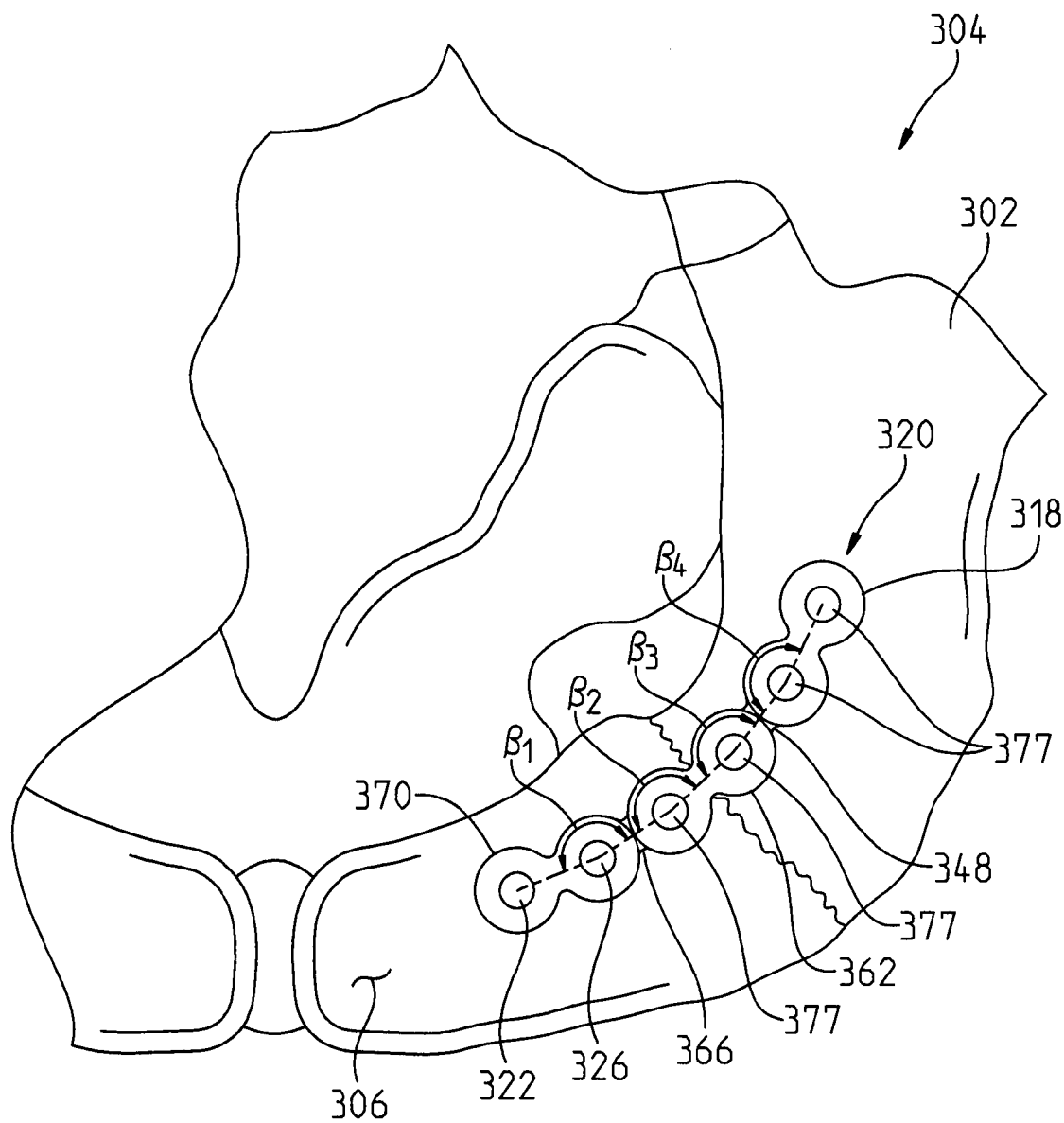
FIG. 28 shows an anterior view of a portion of a human pelvis, showing the bone fixation device of FIG. 22 attached to the pelvis.
Figure 29:
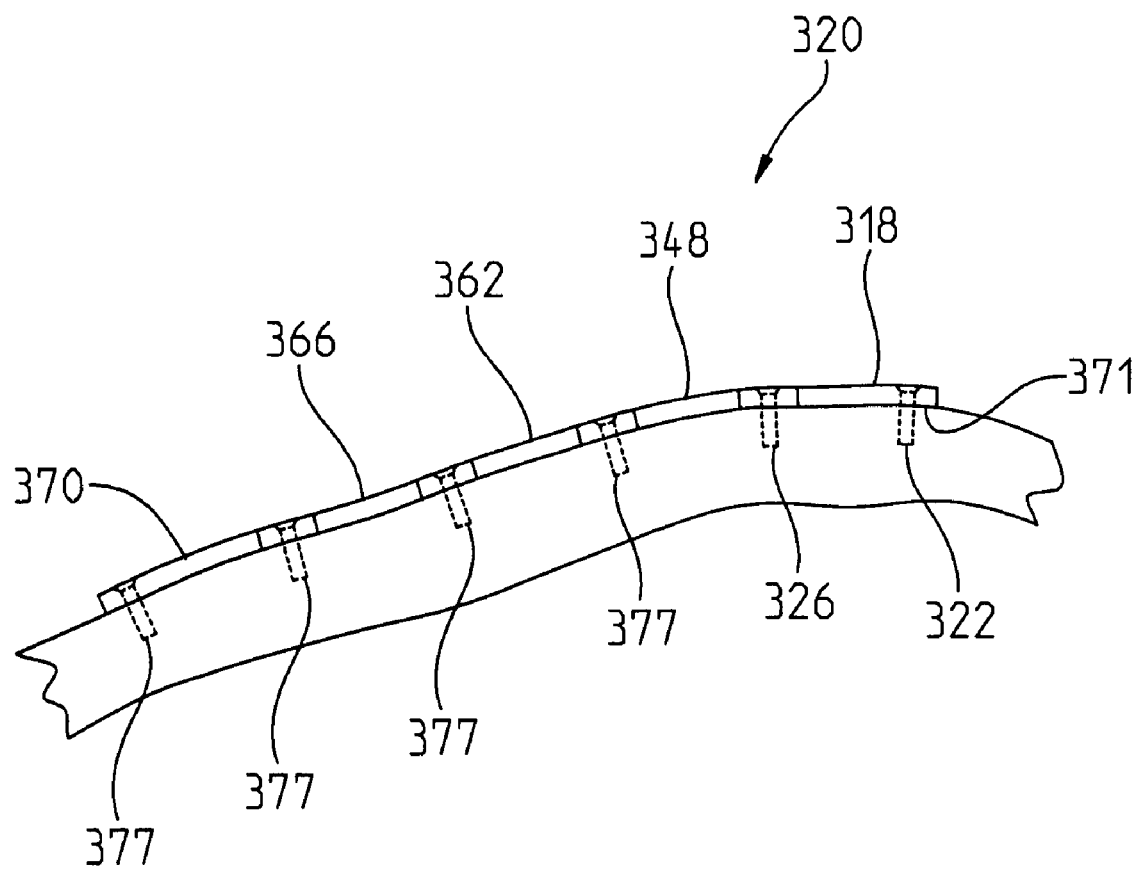
FIG. 29 shows a lateral view of a portion of the human pelvis of FIG. 28 showing the members of the bone fixation device in diverging planes.

Referring now to FIGS. 28 and 29, the bone fixation device 320 is shown in position on a bone 302 in the form of a pelvis of patient 304. The bone fixation device 320 includes first bone fastener 326, second bone fastener 322 and additional bone fasteners 377 that also serve as locking members for the bone fixation device 320. Each construct 318, 348, 362, 366 and 370 is aligned with the bone 302 while the locking members 326, 322 and 377 are in an unlocked condition. The angles $\beta_1$ through $\beta_4$ may then be adjusted to properly align the bone fixation device 320 with the pelvis 2. When properly aligned, the lower surface 371 of the bone fixation device 320 typically rests in mating contact with surface 306 of the pelvis 302.

Figure 30:
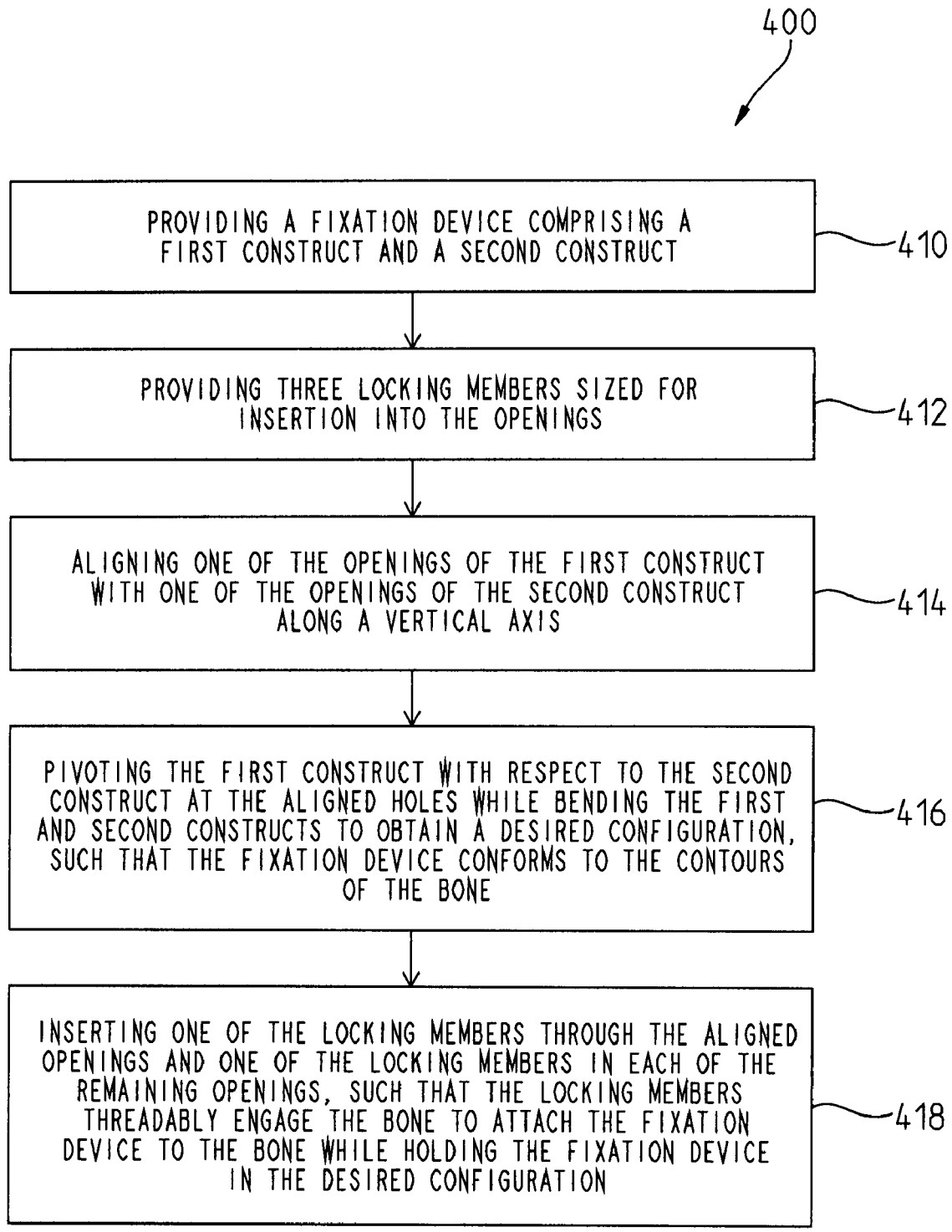
FIG. 30 shows a flow diagram for a method of performing surgery.

According to the present disclosure and referring now to FIG. 30, another embodiment of the present disclosure is in the form of surgical procedure or method 400. The method 400 is utilized for stabilizing a damaged bone of a patient. The method includes a step 410 of providing a fixation device comprising a first construct and a second construct, wherein each of the first and second constructs include a plurality of stacked, flexible members, and wherein each of the first and second constructs have opposing ends defining an opening. The method also includes a step 412 of providing three locking members sized for insertion into the openings, wherein each locking member includes threads for engagement into the bone. The method also includes a step 414 of aligning one of the openings of the first construct with one of the openings of the second construct along a vertical axis. The method also includes a step 416 of pivoting the first construct with respect to the second construct at the aligned holes while bending the first and second constructs to obtain a desired configuration, such that the fixation device conforms to the contours of the bone. The method also includes a step 418 of inserting one of the locking members through the aligned openings and one of the locking members in each of the remaining openings, such that the locking members threadably engage the bone to attach the fixation device to the bone while holding the fixation device in the desired configuration. The method may also include pivoting the first constructs relative to each other in an x-y plane or twisting the constructs around an x axes.

Figure 31:
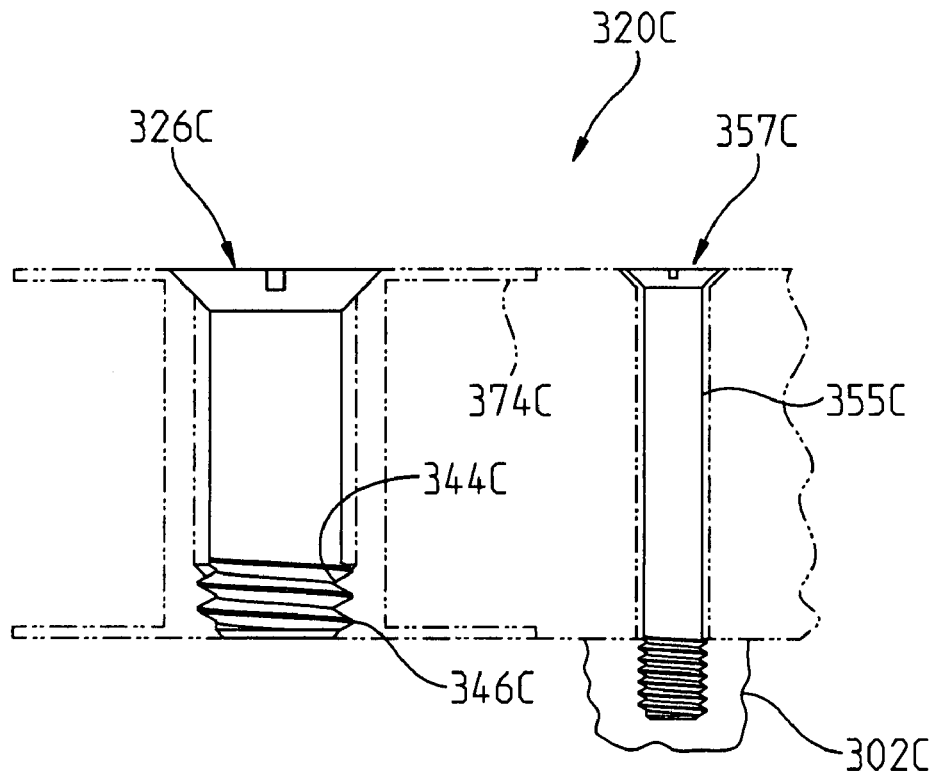
FIG. 31 shows a partial plan view, partially in cross section, of another embodiment of a flexible bone fixation device of the present disclosure utilizing separate locking member and bone fasteners.
Figure 32:
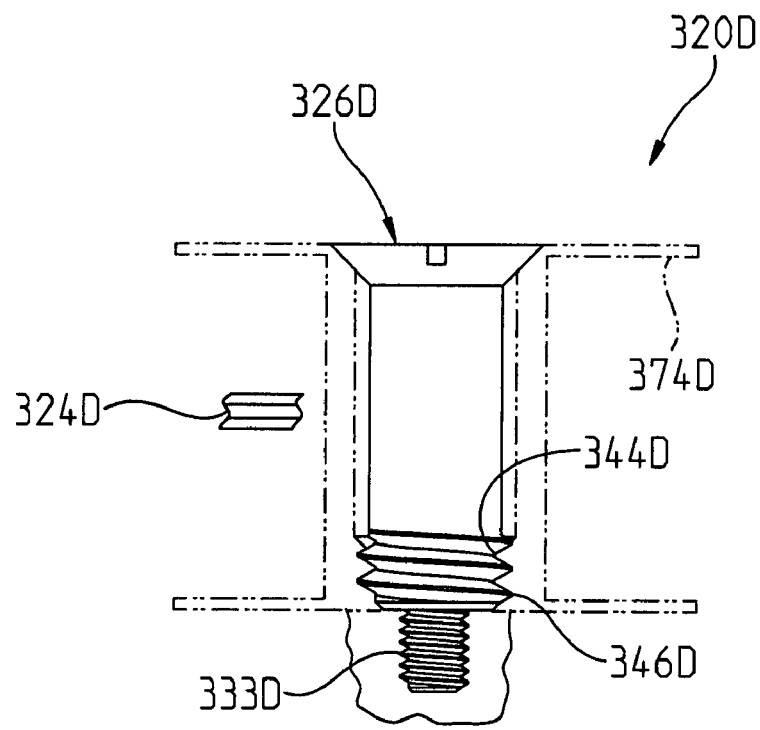
FIG. 32 shows a partial plan view, partially in cross section, of yet another embodiment of a flexible bone fixation device of the present disclosure utilizing a locking member with different size locking threads and bone threads.
Figure 33:
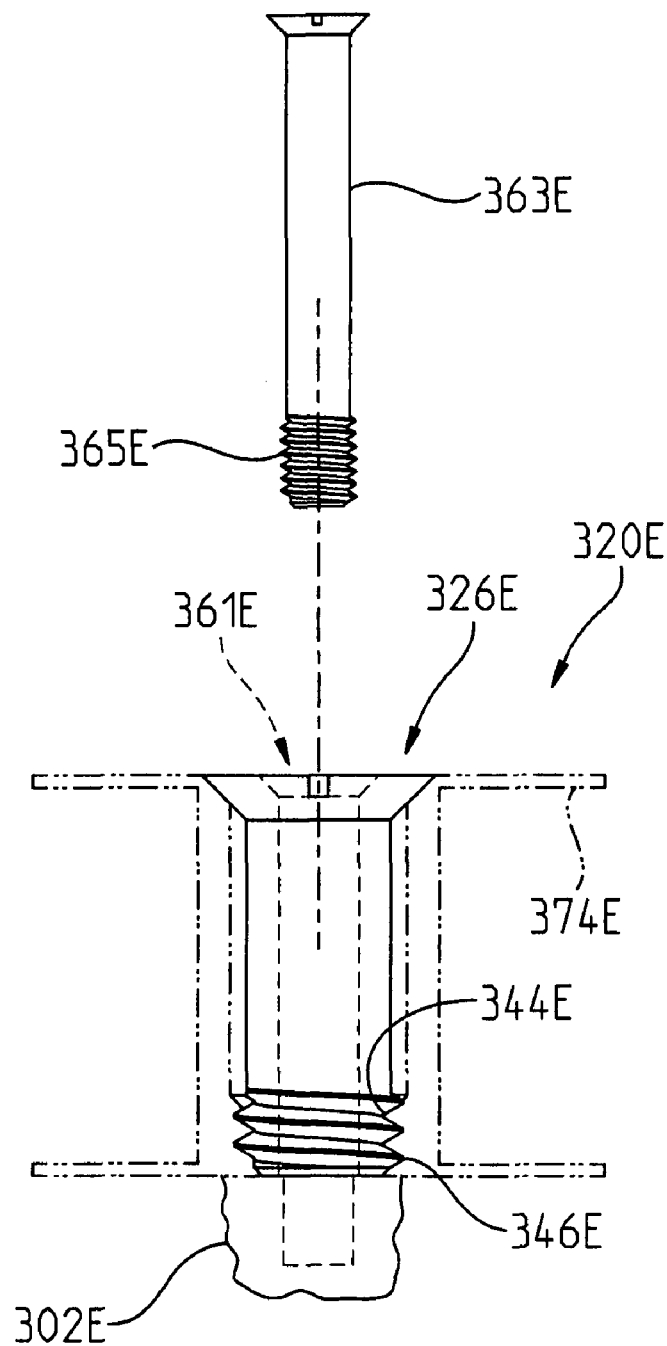
FIG. 33 shows a partial plan view, partially in cross section, of another embodiment of a flexible bone fixation device of the present disclosure utilizing a separate bone fastener fitting inside a cannulated separate locking member.

Referring now to FIGS. 31-33, alternate configurations of the locking member of the present disclosure are shown. Referring to FIG. 32, locking member 326C is shown for use in bone fixation device 320C. The bone fixation device 320C is similar to the bone fixation device 320 of FIGS. 22-29 except that the bone fixation device 320C includes locking member 326C which does not include bone threads. The locking member 326 includes external locking threads 346C which mate with internal threads 344C formed on retainer 374C. A bone fastener 355C fitted into an additional opening 357C formed in device 320C is utilized to secure the bone fixation device 320C to bone 302C. It should be appreciated that the bone fixation device 320C may provide for radial compression of the bone fixation device 320C against bone 302C.

Referring now to FIG. 32, another embodiment of this disclosure is shown as bone fixation device 320D. The bone fixation device 320D includes a first locking member 326D to secure the plurality of plates 324D together. The first locking member 326D includes external locking threads 346D which mate with internal threads 344D formed on retainer 374D. The first locking member 326D further includes bone threads 333D which are smaller than the locking threads 346D of the first locking member 326D of the bone fixation device 320D. It should be appreciated that the bone threads 333D may be cortical or cancellous threads. If the pitch of the bone threads 333D is greater than the pitch of the external threads 346D, the device 320D may provide radial compression.

Referring now to FIG. 33, yet another embodiment of the present invention is shown as bone fixation device 320E. The bone fixation device 320E includes a first locking member 326E which is cannulated to provide a longitudinal opening 361E for receiving a separate bone screw 363E through the opening 361E. The first locking member 326E includes external locking threads 346E which mate with internal threads 344E formed on retainer 374E. It should be appreciated that the bone screws 363E may include external bone threads 365E which are cortical or cancellous threads. It should further be appreciated that the bone screw 363E provides for radial compression of bone 302E.

In the above-described embodiments, the surfaces of the flexible members or laminates may be treated or provided with any one of numerous processes, coatings, or features to enhance the frictional lock achievable when fixed together in the rigid condition. For example, the surfaces of the flexible members may be provided with a rough texture, such as may be obtained by sand blasting, or a multiplicity of tiny projections, teeth, serrations, or other structural features. A bonding agent such as a moisture activated cement or glue may be coated or otherwise disposed on the surfaces of the flexible members, such that once the implant is placed in the wet environment of the body, the bonding agent becomes active, and cures fully several minutes or hours later to increase the rigidity of the construct. The bonding agent may also be activated by heat, UV radiation, or other energy source.

Although the present invention has been described with respect to certain preferred embodiments, it will be appreciated by those of skill in the art that other implementations and adaptations are possible. For example, although the flexible members disclosed herein have been shown stacked in a vertical fashion, the flexible members may also be positioned laterally relative to one another. In addition, the shapes of the locking members and the flexible members may vary according to the desired surgical application. For example, the locking members 26 shown in FIG. 1 may be longer, wider, circular, T-shaped, L-shaped, or shaped otherwise such that the bone fixation device may be better adapted to match the patient's anatomy. Or, for example, the fixation device 120 shown in FIG. 17 may be provided without a head portion, such that the device is more appropriate for fixation of a long bone fracture. Of course, numerous other adaptations are possible. Moreover, there are advantages to individual advancements described herein that may be obtained without incorporating other aspects described above. Therefore, the spirit and scope of the appended claims should not be limited to the description of the preferred embodiments contained herein.

What is claimed is:

1. A bone fixation device comprising:
a first construct comprising a plurality of first flexible plates, wherein the plurality of first flexible plates are configured to bend when a first threshold force is applied to said first construct and the plurality of first flexible plates are in an unlocked relationship, said first construct including a first middle portion located about half-way between a first end portion of the first construct and a second end portion of the first construct opposite to the first end portion;
a second construct comprising a plurality of second flexible plates, wherein the plurality of second flexible plates are configured to bend when a second threshold force is applied to said second construct and the plurality of second flexible plates are in an unlocked relationship, said second construct (i) including a second middle portion located about half-way between a third end portion of the second construct and a fourth end portion of the second construct opposite to the third end portion, and (ii) only partially overlapping said first construct such that the first middle portion does not overlap the second middle portion; and
a first locking member configured to compress an overlapped portion of the plurality of first flexible plates and an overlapped portion of the plurality of second flexible plates together into a first locked relationship, wherein the first threshold force applied to said first construct and the second threshold force applied to said second construct is insufficient to bend the plurality of first flexible plates and the plurality of second flexible plates in the first locked relationship.

2. The bone fixation device of claim 1, further comprising:
a second locking member configured to compress the plurality of first flexible plates together into a second locked relationship, wherein the first threshold force applied to said first construct is insufficient to bend the plurality of first flexible plates in the second locked relationship; and
a third locking member configured to compress the plurality of second flexible plates together into a third locked relationship, wherein the second threshold force applied to said second construct is insufficient to bend the plurality of second flexible plates in the third locked relationship.

3. The bone fixation device of claim 1, further comprising a retainer, said retainer comprising:
a first retaining portion having a first surface configured for cooperation with one of the plurality of first flexible plates; and
a second retaining portion connected to the first retaining portion, the second retaining portion having a second surface configured for cooperation with a second of the plurality of first flexible plates, the plurality of first flexible plates positioned between the first surface and the second surface.

4. The bone fixation device of claim 3, wherein:
the first retaining portion includes a first plate, the first plate defining the first surface; and
the second retaining portion includes a second plate, the second plate defining the second surface.

5. The bone fixation device of claim 3, wherein:
the first retaining portion includes an internal wall defining a first portion opening in the first retaining portion;
the second retaining portion includes an internal wall defining a second portion opening in the second retaining portion; and
said first locking member comprises a bone fastener including a portion fitted to the first portion opening and to the second portion opening.

6. A bone fixation device, comprising:
a first construct comprising a plurality of first flexible members, wherein the plurality of first flexible members are configured to bend when a first threshold force is applied to said first construct and the plurality of first flexible members are in an unlocked relationship;
a retainer retaining the plurality of first flexible members in an assembled relationship, the retainer including a first retaining portion having a first surface configured for cooperation with one of the plurality of first flexible members, and a second retaining portion connected to the first retaining portion, the second retaining portion having a second surface configured for cooperation with an opposed one of the plurality of first flexible members, the plurality of first flexible members positioned between the first surface and the second surface; and
a first locking member configured to apply a force to the retainer to compress the plurality of first flexible members together into a first locked relationship, wherein the first threshold force applied to said first construct is insufficient to bend the plurality of first flexible members in the first locked relationship, wherein:
the first retaining portion includes a tab; and
the second retaining portion includes a groove configured to receive the tab.

7. The bone fixation device of claim 6, further comprising:
a second locking member configured to compress the plurality of first flexible members together into a second locked relationship, wherein the first threshold force applied to said first construct is insufficient to bend the plurality of first flexible members in the second locked relationship.

8. The bone fixation device of claim 6, wherein:
the first retaining portion includes a first plate, the first plate defining the first surface; and
the second retaining portion includes a second plate, the second plate defining the second surface.

9. The bone fixation device of claim 6, wherein:
one of the first retaining portion and the second retaining portion defines an internal thread; and
said first locking member includes an external thread for cooperation with the internal thread, said first locking member being configured to urge the first retaining portion toward the second retaining portion.

10. The bone fixation device of claim 6, wherein:
each of the plurality of first flexible members defines a respective internal wall defining an opening therethrough;
the first retaining portion includes a first retaining portion hub; and
the second retaining portion includes a second retaining portion hub, and the respective internal wall of each of the plurality of first flexible members mates with at least one of the first retaining portion hub and the second retaining portion hub.

11. The bone fixation device of claim 6, wherein the first locking member comprises a threaded fastener.

12. The bone fixation device of claim 11, wherein each of the plurality of first flexible members comprises a respective internal wall defining a first member first opening, at least one of the first member first openings including a thread for cooperation with the threaded fastener.

13. The bone fixation device of claim 11, wherein the threaded fastener includes bone threads.

14. A bone fixation device, comprising:
a first construct comprising a plurality of first flexible members, wherein the plurality of first flexible members are configured to bend when a first threshold force is applied to said first construct and the plurality of first flexible members are in an unlocked relationship;
a retainer retaining the plurality of first flexible members in an assembled relationship, the retainer including a first retaining portion having a first surface configured for cooperation with one of the plurality of first flexible members, and a second retaining portion connected to the first retaining portion, the second retaining portion having a second surface configured for cooperation with an opposed one of the plurality of first flexible members, the plurality of first flexible members positioned between the first surface and the second surface; and
a first locking member configured to apply a force to the retainer to compress the plurality of first flexible members together into a first locked relationship, wherein the first threshold force applied to said first construct is insufficient to bend the plurality of first flexible members in the first locked relationship, wherein:
the first retaining portion includes a internal wall defining a first portion opening in the first retaining portion;
the second retaining portion includes an internal wall defining a second portion opening in the second retaining portion; and
said first locking member comprises a bone fastener including a portion fitted to the first portion opening and to the second portion opening.

15. The bone fixation device of claim 14:
further comprising a second construct comprising a plurality of second flexible members, only a first portion of each of the plurality of second flexible members overlapping a second portion of each of the plurality of first flexible members, wherein the plurality of second flexible members are configured to bend when a second threshold force is applied to said second construct and the plurality of second flexible members are in an unlocked relationship; and
wherein said first locking member is configured to compress the plurality of second flexible members together into a second locked relationship, wherein the second threshold force applied to said second construct is insufficient to bend the plurality of second flexible members in the second locked relationship.

16. The bone fixation device of claim 15:
wherein the plurality of first flexible members comprise plates; and
wherein the plurality of second flexible members comprise plates.

17. The bone fixation device of claim 15, wherein the plurality of second flexible members are interleaved with the plurality of first flexible members.

18. The bone fixation device of claim 15:
wherein each of the plurality of first flexible members comprises a first internal wall, each of the first internal walls defining a first member first opening;
wherein each of the plurality of first flexible members comprises a second internal wall, each of the second internal walls defining a first member second opening;
wherein each of the plurality of second flexible members comprises a first internal wall, each of the first internal walls defining a second member first opening;
wherein each of the plurality of second flexible members comprises a second internal wall, each of the second internal walls defining a second member second opening; and
wherein said first locking member is configured to cooperate with each of said first member first openings and said second member first openings.

19. The bone fixation device of claim 18:
further comprising a second locking member configured to cooperate with each of the first member second openings; and
further comprising a third locking member configured to cooperate with each of the second member second openings.

20. The bone fixation device of claim 18, wherein at least one of the first member second openings is threaded.

21. The bone fixation device of claim 15, wherein each of the plurality of first flexible members is similar in size and shape to each of the plurality of second flexible members.

22. The bone fixation device of claim 15, further comprising:
a third construct comprising a plurality of third flexible members, only a third portion of each of the plurality of third flexible members overlapping a fourth portion of each of the plurality of second flexible members, the plurality of third flexible members configured to bend when a third threshold force is applied to said third construct and the plurality of third flexible members are in an unlocked relationship, wherein the plurality of third flexible members comprise plates; and
a second locking member configured to compress the plurality of third flexible members and the plurality of second flexible members together into a third locked relationship, wherein the third threshold force applied to said third construct and said second threshold force applied to said second construct are insufficient to bend the plurality of second flexible members and the plurality of third flexible members in the third locked relationship.

23. The bone fixation device of claim 22, wherein the plurality of third flexible members are interleaved with the plurality of second flexible members.

24. The bone fixation device of claim 22, wherein one of the second flexible members is placed between adjacent third flexible members and wherein one of the third flexible members is placed between adjacent second flexible members.

25. The bone fixation device of claim 22:
wherein said first locking member defines a longitudinal axis thereof;
wherein said second locking member defines a longitudinal axis thereof; and
wherein the longitudinal axis of said first locking member and the longitudinal axis of said second locking member are skewed with respect to each other.

* * * * *

UNITED STATES PATENT AND TRADEMARK OFFICE
CERTIFICATE OF CORRECTION

PATENT NO. : 8,114,080 B2
APPLICATION NO. : 11/900896
DATED : February 14, 2012
INVENTOR(S) : Dale R. Schulze Page 1 of 2

It is certified that error appears in the above-identified patent and that said Letters Patent is hereby corrected as shown below:

Title Page, item (57), Abstract,
Line 1, delete second occurrence of "bone fixation device"

Column 1,
Lines 30-32, delete first paragraph [0004] "One type of bone plate for acetabular and other pelvic fractures is called a reconstruction bar. Conventional reconstruction bars are generally formed from a"

Column 3,
Lines 3-4, delete second occurrence of "bone fixation device"

Column 3,
Line 25, after "relationship" delete "bone"

Column 3,
Line 30, after "relationship" insert --.--

Column 4,
Line 66, replace "plain view" with --plan view--

Column 6,
Line 2, replace "provided my" with --provided by--

Column 6,
Line 23, after "locking members 26" delete "are"

Column 8,
Line 42, replace "an unlocked" with --a locked--

Signed and Sealed this
Twenty-sixth Day of March, 2013

Teresa Stanek Rea
*Acting Director of the United States Patent and Trademark Office*

CERTIFICATE OF CORRECTION (continued)
U.S. Pat. No. 8,114,080 B2

Column 11,
Line 18, replace "use" with --uses--

Column 11,
Line 40, replace "formed form" with --formed from--

Column 11,
Line 55, replace "design" with --designed--

Column 23,
Line 23, replace "a internal wall" with --an internal wall--